(12) United States Patent
Song et al.

(10) Patent No.: US 11,413,313 B2
(45) Date of Patent: *Aug. 16, 2022

(54) PHARMACEUTICAL COMPOSITION FOR PREVENTING OR TREATING ATOPIC DERMATITIS COMPRISING CLONAL STEM CELLS

(71) Applicant: SCM LIFESCIENCE CO., LTD., Incheon (KR)

(72) Inventors: Sun Uk Song, Incheon (KR); Si Na Kim, Incheon (KR); Jeong Hyun Moon, Incheon (KR)

(73) Assignee: SCM LIFESCIENCE CO., LTD., Incheon (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/992,825

(22) Filed: Aug. 13, 2020

(65) Prior Publication Data
US 2020/0384035 A1 Dec. 10, 2020

Related U.S. Application Data

(63) Continuation of application No. 16/631,575, filed as application No. PCT/KR2019/018089 on Dec. 19, 2019.

(60) Provisional application No. 62/793,022, filed on Jan. 16, 2019.

(51) Int. Cl.
*A61K 35/28* (2015.01)
*A61P 17/18* (2006.01)
*C12N 5/0775* (2010.01)

(52) U.S. Cl.
CPC .............. *A61K 35/28* (2013.01); *A61P 17/18* (2018.01); *C12N 5/0663* (2013.01)

(58) Field of Classification Search
CPC ........ A61K 35/28; A61P 17/18; C12N 5/0663
See application file for complete search history.

(56) References Cited

U.S. PATENT DOCUMENTS 8,796,020 B2 * 8/2014 Song ................ A01N 37/46
435/374

FOREIGN PATENT DOCUMENTS

KR 20150065147 A * 6/2015 ............. A61K 35/50

OTHER PUBLICATIONS

Williams et al. Prevention of atopic dermatitis. F1000 Medicine Reports 2012, 4:24. p. 1-5 (Year: 2012).*
Daltro et al. Mesenchymal Stem Cells and Atopic Dermatitis: A Review. Frontiers in Cell and Developmental Biology. May 2020, vol. 8, Article 326, p. 1-10 (Year: 2020).*
Rajkumar et al. The State of Prevention in Atopic Dermatitis. Practical Dermatology. Sep. 2019, p. 67-71 (Year: 2019).*
Karystinou et al. Distinct mesenchymal progenitor cell subsets in the adult human synovium. Rheumatology 2009;48:1057-1064 (Year: 2009).*
Alves et al. Effect of Antioxidant Supplementation on the Total Yield, Oxidative Stress Levels, and Multipotency of Bone Marrow-Derived Human Mesenchymal Stromal Cells. Tissue Engineering: Part A vol. 19, Nos. 7 and 8. p. 928-937 (Year: 2013).*
Fossett et al. Effect of Age and Gender on Cell Proliferation and Cell Surface Characterization of Synovial Fat Pad Derived Mesenchymal Stem Cells. J Orthop Res 30:1013-1018 (Year: 2012).*
Denu et al. Effects of Oxidative Stress on Mesenchymal Stem Cell Biology. Oxidative Medicine and Cellular Longevity vol. 2016, Article ID 2989076, 9 pages (Year: 2016).*

* cited by examiner

*Primary Examiner* — Taeyoon Kim
(74) *Attorney, Agent, or Firm* — Sughrue Mion, PLLC

(57) ABSTRACT

Disclosed is a composition for prevention, treatment or ameliorating of atopic dermatitis, the composition containing a monoclonal stem cell obtained via improved subfractionation culturing of a stem cell, a preparation method thereof, and a method for treating atopic dermatitis using the same. According to the improved subfractionation culturing and proliferation method of the stem cell, a desired amount of the monoclonal stem cells may be obtained in a massive manner in a short time via the rapid proliferation of the monoclonal stem cell. The monoclonal mesenchymal stem cell as obtained has an enhanced effect of treatment, prevention or ameliorating of atopic dermatitis, and thus may be usefully used for an atopic dermatitis treatment agent.

6 Claims, 41 Drawing Sheets

FIG. 10

| Fold Increase (F.I) | | | |
|---|---|---|---|
| cell/cm² | P11 | P13 | P15 |
| HD | 2.6±0.3 | 1.9±0.2 | 1.6±0.1 |
| HD + AA | 3.8±0.5 | 2.9±0.1 | 2.5±0.2 |

| Relative Proliferation Index | | | |
|---|---|---|---|
| cell/cm² | P11 | P13 | P15 |
| HD | 1 | 1 | 1 |
| HD + AA | 1.46 | 1.52 | 1.58 |

| SCM06 | Item | P1 | P2 | P3 | P4 | P5 |
|---|---|---|---|---|---|---|
| 4000LG | 4000N | | 4 | 3 | 4 | 3 |
| | Fold Increase | 0 | 1.67 | 1.67 | 1.31 | 0.95 |
| | Cell Numbers (x10⁴) | 22.000 | 36.74 | 61.36 | 80.38 | 76.38 |
| 4000alpha | 4000alpha | | 4 | 3 | 4 | 3 |
| | Fold Increase | 0 | 2.14 | 1.83 | 1.25 | 0.71 |
| | Cell Numbers (x10⁴) | 22.000 | 47.00 | 86.18 | 107.70 | 76.46 |
| 1000LG | 1000N | | 7 | 7 | 7 | 7 |
| | Fold Increase | 0 | 7.14 | 5.95 | 4.76 | 3.33 |
| | Cell Numbers (x10⁴) | 5.500 | 39.27 | 233.66 | 1112.70 | 3703.64 |
| 1000alpha | 1000alpha | | 7 | 7 | 7 | 7 |
| | Fold Increase | 0 | 10.00 | 5.71 | 5.00 | 4.17 |
| | Cell Numbers (x10⁴) | 5.500 | 55.00 | 314.05 | 1579.25 | 6547.94 |

B SCM06

| Population Doubling Time (PDT) | |
|---|---|
| 4000LG | 7.80 |
| 4000alpha | 7.79 |
| 1000LG | 2.98 |
| 1000alpha | 2.74 |

| Population Doubling Level (PDL) | |
|---|---|
| 4000LG | 2.54 |
| 4000alpha | 1.80 |
| 1000LG | 9.40 |
| 1000alpha | 10.22 |

| SCM08 | Item | P1 | P2 | P3 | P4 | P5 |
|---|---|---|---|---|---|---|
| 4000LG | 4000N | | 4 | 3 | 4 | 3 |
| | Fold Increase | 0 | 3.14 | 3.00 | 2.82 | 1.41 |
| | Cell Numbers (x10⁴) | 22.000 | 69.08 | 207.24 | 584.42 | 823.83 |
| 4000alpha | 4000alpha | | 4 | 3 | 4 | 3 |
| | Fold Increase | 0 | 4.00 | 3.87 | 3.36 | 3.64 |
| | Cell Numbers (x10⁴) | 22.000 | 88.00 | 340.56 | 1144.28 | 4165.19 |
| 1000LG | 1000N | | 7 | 7 | 7 | 7 |
| | Fold Increase | 0 | 6.18 | 6.36 | 5.55 | 4.55 |
| | Cell Numbers (x10⁴) | 5.500 | 33.99 | 216.18 | 1199.78 | 5458.99 |
| 1000alpha | 1000alpha | | 7 | 7 | 7 | 7 |
| | Fold Increase | 0 | 9.27 | 8.45 | 8.00 | 7.64 |
| | Cell Numbers (x10⁴) | 5.500 | 50.99 | 430.82 | 3446.59 | 26331.92 |

| Population Doubling Time (PDT) | |
|---|---|
| 4000LG | 2.68 |
| 4000alpha | 1.85 |
| 1000LG | 2.81 |
| 1000alpha | 2.29 |

| Population Doubling Level (PDL) | |
|---|---|
| 4000LG | 6.88 |
| 4000alpha | 7.56 |
| 1000LG | 9.96 |
| 1000alpha | 12.23 |

| Cell Name | | A0108 | | | | | | | |
| --- | --- | --- | --- | --- | --- | --- | --- | --- | --- |
| | | SCM01 | SCM02 | SCM03 | SCM04 | SCM05 | SCM06 | SCM07 | SCM08 |
| POT | 4000LG | 5.05 | 3.99 | 2.44 | 4.96 | 5.16 | 7.80 | 3.77 | 2.68 |
| | 1000LG | 3.20 | 3.93 | 2.57 | 3.61 | 3.40 | 2.98 | 2.56 | 2.81 |
| PDL | 4000LG | 3.84 | 5.12 | 7.55 | 4.18 | 4.42 | 2.54 | 5.21 | 6.88 |
| | 1000LG | 8.74 | 7.13 | 10.89 | 7.75 | 8.23 | 9.40 | 10.96 | 9.96 |

| Cell Name | | A0106 | | | | | | | |
|---|---|---|---|---|---|---|---|---|---|
| | | SCM01 | SCM02 | SCM03 | SCM04 | SCM05 | SCM06 | SCM07 | SCM08 |
| PDT | 4000alpha | 3.11 | 4.47 | 2.14 | 4.83 | 2.94 | 7.79 | 4.08 | 1.85 |
| | 1000alpha | 2.72 | 3.11 | 2.33 | 3.17 | 2.57 | 2.74 | 2.43 | 2.29 |
| PDL | 4000alpha | 4.50 | 3.13 | 6.54 | 2.90 | 4.76 | 1.80 | 3.43 | 7.56 |
| | 1000alpha | 10.28 | 9.00 | 12.01 | 8.84 | 10.90 | 10.22 | 11.52 | 12.23 |

| Cell Name | | A0108 | | | | | | | |
|---|---|---|---|---|---|---|---|---|---|
| | | SCM01 | SCM02 | SCM03 | SCM04 | SCM05 | SCM06 | SCM07 | SCM08 |
| PDT | 1000LG | 3.20 | 3.93 | 2.57 | 3.61 | 3.40 | 2.96 | 2.56 | 2.81 |
| | 1000alpha | 2.72 | 3.11 | 2.33 | 3.17 | 2.57 | 2.74 | 2.43 | 2.29 |
| PDL | 1000LG | 8.74 | 7.13 | 10.89 | 7.75 | 8.23 | 9.40 | 10.96 | 9.96 |
| | 1000alpha | 10.28 | 9.00 | 12.01 | 8.84 | 10.90 | 10.22 | 11.82 | 12.23 |

BALB/c mouse dorsal skin lesions of each group. (-): normal control, Veh.: AD+PBS

PHARMACEUTICAL COMPOSITION FOR PREVENTING OR TREATING ATOPIC DERMATITIS COMPRISING CLONAL STEM CELLS

CROSS-REFERENCES TO RELATED APPLICATIONS

This application is a Continuation of U.S. patent application Ser. No. 16/631,575 filed on Jan. 16, 2020, which is a U.S. national phase application, pursuant to 35 U.S.C. § 371, of PCT/KR2019/018089, filed Dec. 19, 2019, designating the United States, which claims priority to U.S. Provisional Patent Application No. 62/793,022, filed Jan. 16, 2019. The entire contents of the aforementioned patent applications are incorporated herein by this reference.

TECHNICAL FIELD

The present disclosure relates to a composition for prevention, treatment or ameliorating of atopic dermatitis, the composition containing a monoclonal stem cell obtained via improved subfractionation culturing of a stem cell, a preparation method thereof, and a method for treating atopic dermatitis using the same.

BACKGROUND

Atopic dermatitis (AD) also known as atopic eczema, is a very common inflammatory skin disease. It is reported that pathogenesis of acute atopic dermatitis is related to Th2 inflammatory response mediated by CD4+T cell and eosinophil dermal penetration, and increased secretion of immunoglobulin E (IgE) and Th2 cytokine. Atopic dermatitis is accompanied by severe itching and dry skin. Atopic dermatitis causes high IgE expression in blood and an increase of eosinophils. Recently, it has been estimated that atopic dermatitis occurs in about 10 to 20% of a total population. There is no clear cure for atopic dermatitis. Atopic dermatitis is diagnosed at most of children or babies 5 years old or younger. 50% thereof is diagnosed at babies between 6 and 24 months. Based on a national epidemiological survey conducted by Korean Academy of Pediatric Allergy Respiratory Diseases, prevalence of atopic dermatitis has increased gradually over the past 10 years, and thus social interest thereto increases. 50 to 75% of children with atopic dermatitis show a history of allergic disease that progresses to asthma and rhinitis. Thus, early diagnosis and management of atopic dermatitis at a starting point of allergic progression are very important in preventing adult allergic progression.

Atopic dermatitis is caused by immunological abnormalities such as activation of T lymphocytes, abnormal cytokine system, decreased cell-mediated immunity, and increased IgE, physiological factors, and many other factors such as biochemical defects of a skin. In order to treat the atopic dermatitis, it is necessary to moisturize dry skin and to use drugs such as steroids. As a treatment agent for atopic dermatitis having mild symptoms, moisturizers, topical steroids, antihistamines, antibiotics and topical immune response modifiers may be used. As a treatment agent for severe atopic dermatitis, systemic steroids or immunosuppressants are used. Taking the drug for a long time, and then stop taking the drug may cause a possibility of recurrence of a lesion to be high. Thus, a safe and effective treatment method for long-term use is required.

Recently, attempts have been made to use stem cells in treatment of various inflammatory diseases. Stem cells have potential to grow into tissues of all of 210 organs in a human body, may divide indefinitely, and may differentiate into a target organ via proper engineering. Because of these characteristics of the stem cells, stem cells are in a spotlight as new therapeutics. A treatment success possibility of intractable diseases using the stem cells is very high. Thus, the stem cells are expected to be able to treat many diseases such as leukemia, osteoporosis, hepatitis, Parkinson's disease, senile dementia and burns.

However, stem cells still have many limitations in that it may be difficult to obtain the stem cells in large quantities. A method of obtaining the stem cells from frozen embryonic cells is efficient. However, this approach causes still much controversy in terms of ethics. In order to solve such a problem, a number of studies have been conducted to obtain a stem cell using a somatic-cell nuclear transplant method or an adult stem cell. The study of the adult stem cells is conducted more vigorously than the study of embryonic stem cells. Adult stem cells remain in various organs such as a central nervous system and bone marrow, and are involved in organ development during growth and in regeneration of damage tissues. Thus, the adult stem cell may be obtained from various parts such as bone marrow, spleen, fat cell, etc. In this connection, a method for the adult stem cells from the bone marrow is most often performed. However, it is difficult to always obtain uniform cells in isolation and culturing of monoclonal mesenchymal stem cells among many different types of bone marrow cells. Thus, a research is in progress to solve this problem The present inventors invented a novel method of isolation of stem cells referred to as a subfractionation culturing method. This method was filed to have Korean Patent Application No. 10-2006-0075676 which in turn is allowed in terms of patentability. The subfractionation culturing method is less expensive than other methods and is excellent in comparison with other stem cell obtaining methods in that clonal mesenchymal stem cells (cMSCs) may be obtained effectively by the subfractionation culturing method without contamination problems, while other stem cells are not mixed with a target stem cell. However, despite the superiority of the subfractionation culturing method, the subfractionation culturing method requires preparing working cell banks and obtaining final products therefrom, for mass production of mesenchymal stem cells and using the mesenchymal stem cells as final products, thereby obtaining enough mesenchymal stem cells. In this connection, the subfractionation culturing method may not rapidly obtain a monoclonal mesenchymal stem cell population because a culturing of at least 10 passages is required.

Therefore, the use of the stem cells to treat inflammatory diseases, especially atopic dermatitis, has various limitations. There is no known stem cell preparation method for effectively treating atopic dermatitis and no known atopic dermatitis treatment method using the same.

SUMMARY

The present inventors are working to induce rapid proliferation of stem cells via an improved subfractionation culturing method. In this process, we confirmed that using the improved subfractionation culturing method in which a cultured cell density is low and antioxidant is added may induce effectively an increase in a cell proliferation rate using only a small number of culture passages; and the monoclonal stem cell obtained in this manner is found to have a more significant atopic dermatitis treatment effect than a stem cell obtained from the conventional subfractionation culturing method. In this way, the present disclosure was completed.

Therefore, a purpose of the present disclosure is to provide a composition for prevention, treatment and ameliorating of atopic dermatitis, the composition containing a monoclonal stem cell obtained using a subfractionation culturing and proliferation method of a stem cell that is improved over the conventional subfractionation culturing method, to provide a preparation method thereof, and a method for preventing, treating and ameliorating of atopic dermatitis using the same.

One aspect of the present disclosure provides a pharmaceutical composition for prevention or treatment of atopic dermatitis, the composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

Further, another aspect of the present disclosure provides a cosmetic composition for prevention or ameliorating of atopic dermatitis, the composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

Further, still another aspect of the present disclosure provides a quasi-drug composition for prevention or ameliorating of atopic dermatitis, the composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

Furthermore, still yet another aspect of the present disclosure provides a method for preparing a composition for prevention, treatment, or ameliorating of atopic dermatitis, the method including: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein, thereby obtaining the monoclonal stem cell.

Furthermore, still yet another aspect of the present disclosure provides a method for preventing, treating, or ameliorating atopic dermatitis, the method including: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; 5) seeding the monoclonal stem cell in the step 4) into a culture medium at a cell density of 50 to 1000 cells/cm$^2$ and culturing the monoclonal stem cell therein, thereby obtaining the monoclonal stem cell; and 6) administering the monoclonal stem cell to an individual.

Furthermore, still yet another aspect of the present disclosure provides a stem cell for preventing, treating, or ameliorating atopic dermatitis, the stem cell being obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; 5) seeding the monoclonal stem cell in the step 4) into a culture medium at a cell density of 50 to 1000 cells/cm$^2$ and culturing the monoclonal stem cell therein.

Another aspect of the present disclosure provides a method for preventing or treating atopic dermatitis comprising administering a pharmaceutical composition to a subject, the pharmaceutical composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

Yet another aspect of the present disclosure provides a method for preventing or ameliorating atopic dermatitis comprising administering a cosmetic composition to a subject, the cosmetic composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

Still yet another aspect of the present disclosure provides a method for preventing or ameliorating atopic dermatitis comprising administering a quasi-drug composition to a subject, the quasi-drug composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

According to the improved subfractionation culturing and proliferation method of the stem cell according to the present disclosure, a desired amount of the monoclonal stem cells may be obtained in a massive manner in a short time via the rapid proliferation of the monoclonal stem cell. The monoclonal mesenchymal stem cell as obtained has an enhanced effect of treatment, prevention or ameliorating of atopic dermatitis, and thus may be usefully used for an atopic dermatitis treatment agent.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 7A illustrates the results of identifying the differentiation capacity of monoclonal mesenchymal stem cells into lipocytes through Oil red O histological staining according to cell culture density and cell culture passage; FIG. 7B is a view illustrating the results of quantifying the level of histological staining described FIG. 7A; FIG. 7C illustrates the results of identifying the differentiation capacity of monoclonal mesenchymal stem cells into osteogenic cells through Alizarin red S histological staining according to cell culture density and cell culture passage; FIG. 7D is a view illustrating the results of quantifying the level of histological staining described in FIG. 7C.

FIG. 10 illustrates the results of identifying the changes in the proliferation ability of cells obtained by culturing the monoclonal mesenchymal stem cells of passages 11 to 15 under the condition of only high density (HD) and high density+ascorbic acid (as the antioxidant) addition (HD+AA).

DETAILED DESCRIPTION

Figure 1:
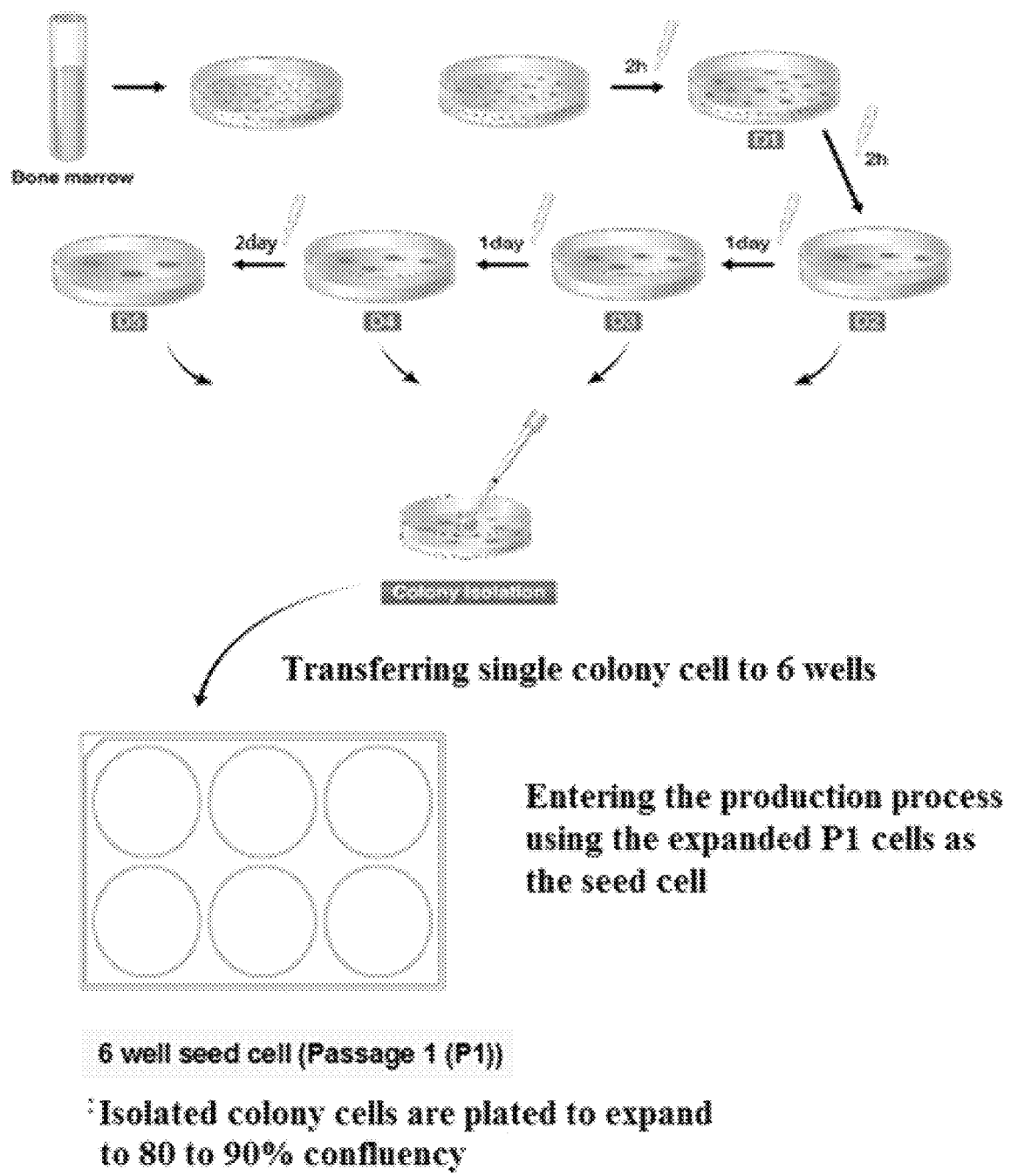
FIG. 1 is a view of illustrating a conventional subfractionation culturing method for isolating monoclonal mesenchymal stem cells from bone marrow.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented herein.

The present disclosure provides a method for preventing or treating atopic dermatitis, the method including administering, to an individual, a pharmaceutical composition containing the monoclonal stem cells obtained via the improved subfractionation culturing and proliferation method of mesenchymal stem cells, or administering the monoclonal stem cells to the individual in need thereof.

Further, the present disclosure provides a preparation method of a composition for preventing, ameliorating or treating the atopic dermatitis, the method including obtaining the monoclonal stem cell via the improved subfractionation culturing and proliferation method of mesenchymal stem cells.

The monoclonal stem cell as an active ingredient according to the present disclosure may be obtained using the subfractionation culturing method quickly and without contamination. Further, the monoclonal stem cell as an active ingredient according to the present disclosure may be obtained via the improved subfractionation culturing method in which the rapid proliferation of the monoclonal stem cells, preferably, the monoclonal mesenchymal stem cells allows desired large quantities of the monoclonal stem cells to be obtained in a short time without a Working Cell Bank (WCB) preparation step. The monoclonal stem cell obtained via the above improved method has an increase in the effect of treating atopic dermatitis as compared with the stem cell obtained via the conventional subfractionation culturing method.

Hereinafter, the present disclosure will be described in detail.

The present disclosure provides a pharmaceutical composition for prevention or treatment of atopic dermatitis, the composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

Cultivation of each of the steps 2) and 3) is performed at 30 to 40° C. for 4 hours or less, preferably, 1 hour to 3 hours, more preferably, 1 hour 30 minutes to 2 hours 30 minutes. The repeated culturing is configured such that a first culturing is performed at 30 to 40° C. for 4 hours or less, preferably 1 hour to 3 hours, more preferably 1 hour 30 minutes to 2 hours 30 minutes, and then a second culturing is performed for 12 to 36 hours at 30 to 40° C., preferably, for 18 to 30 hours. The number of the repetitions of the second culturing may be 2 to 3. Then, a third culturing is performed at 30 to 40° C. for 24 to 72 hours, preferably 36 hours to 60 hours. In each of the first to third culturing, the supernatant may be transferred to a new culturing vessel.

The method in accordance with an embodiment according to the present disclosure is briefly summarized as follows.

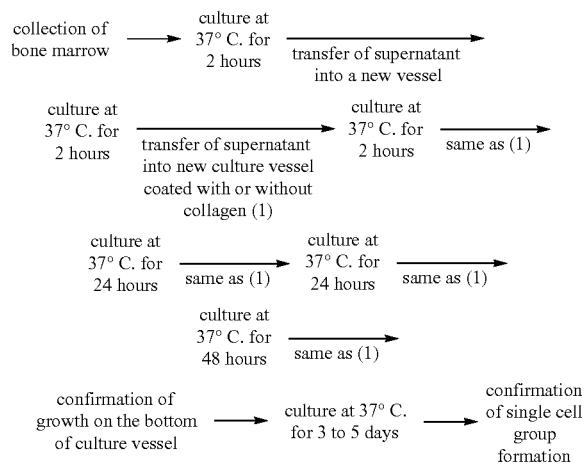

The cultured cells form a monoclonal cell group, which may then be isolated and subcultured. The method in accordance with the present disclosure is characterized by further including the 5) subculturing step in addition to the steps of the conventional subfractionation culturing method.

The term "subfractionation culturing method (SCM)" used herein refers to a method of isolating stem cells according to specific gravity, indicating a process in that first, human bone marrow is extracted and cultured in a cell culture medium, then, only a supernatant is obtained, transferred to a culture vessel with or without treatment of a coating agent, and cultured, and then the processes as described above are repeated several times. Such a subfractionation culturing method is characterized by repeatedly obtaining and culturing the supernatant without centrifugation. It is advantageous that monoclonal stem cells, preferably monoclonal mesenchymal stem cells may be obtained without contamination of other cells finally.

The steps 1) to 4) among the steps 1) to 5) may be performed in the same method as the subfractionation culturing method described in Korean Patent Application No. 10-2006-0075676, or Korean Patent Application No. 10-2014-0170045. Korean Patent Application No. 10-2006-0075676 may be incorporated herein in its entirety by reference.

Further, the Korean Patent Application No. 10-2014-0170045 discloses a subfractionation culturing method for obtaining a cell in connection with the treatment of atopic dermatitis, the method comprising: (i) culturing a sample containing bone marrow-derived mesenchymal stem cells in a first vessel to obtain a first supernatant; (ii) transferring the first supernatant of the first vessel to a second vessel; (iii) culturing cells present in the second vessel to obtain a second supernatant; (iv) repeating the steps (ii) and (iii) three or more times; (v) isolating single cell-derived colonies; and (vi) transferring the cells from the colonies to a growth medium and culturing the cells therein. Thus, the clonal stem cell may be obtained using the subfractionation culturing method. Further, the Korean Patent Application No. 10-2014-0170045 discloses a method for preventing or treating atopic dermatitis using the same. The conventional subfractionation culturing method as disclosed KR 10-2006-0075676 obtains the monoclonal stem cells only using the density difference without using the centrifugal isolation.

However, the KR 10-2006-0075676 and KR10-2014-0170045 fails to disclose a subfractionation culturing method for effectively obtaining the monoclonal stem cells at low passage and a method for significantly improving the treatment effect of atopic dermatitis using the monoclonal stem cells thus obtained.

The conventional subfractionation culturing method, as identified in FIG. 1, transfers all cells obtained from a single colony to 6 wells and the cells are proliferated therein to 80 to 90% confluency. Then, high density culturing is performed at 4000 cells/cm$^2$ in order to obtain many cells using the passage 1 (P1) cells in the proliferated state as seed cells without recognition of the density control.

To the contrary, the present disclosure provide an "improved subfractionation culturing method" based on the ability to effectively obtain stem cells that are effective in preventing, treating and amelioration of atopic dermatitis by controlling cell density in culturing subsequent to passage 2. The improved subfractionation culturing method is differed from the conventional subfractionation culturing method in terms of culturing steps after obtaining the seed cells. For example, the improved subfractionation culturing method further includes "5) seeding the monoclonal stem cell in the step 4) into a culture medium at a cell density of 50 to 1000 cells/cm$^2$ and culturing the monoclonal stem cell therein". The improved subfractionation culturing method may induce the proliferation of the monoclonal stem cell in a faster manner than the conventional subfractionation culturing method. Thus, the final product may be obtained quickly using the improved subfractionation culturing method. Preferably, the MCB (Master Cell Bank) may be prepared by culturing the cells to a passage lower than passage 10 such as P2 to P8, and the monoclonal stem cells exhibiting excellent atopic dermatitis prevention or treatment effect may be obtained.

When the monoclonal stem cells are cultured at a high density of 4000 cells/cm$^2$ as in the conventional method, the cell proliferation ability may be markedly decreased, the markers of the mesenchymal stem cells may be changed, and the differentiation ability may be eliminated. Thus, the monoclonal stem cells obtained through the improved subfractionation culturing method may be cultured at a low density or intermediate density, that is, at the cell density of less than 4000 cells/cm$^2$, for example, at the cell density of 3000 cells/cm$^2$ or less, preferably at the cell density of 2000 cells/cm$^2$ or less, more preferably at the cell density of 50 to 1000 cells/cm$^2$.

When monoclonal mesenchymal stem cells are cultured at a cell density of 1000 cells/cm$^2$ or less, the cell proliferation ability is remarkably high over an extended period of culture compared with mesenchymal stem cells cultured at a high density of 4000 cells/cm$^2$. Thus, it provides an advantage that a large amount of monoclonal cells which is desired may be rapidly obtained without repeating a large number of passages. Therefore, the improved subfractionation culturing method according to the present disclosure may be characterized by performing the subculturing step after the seed cell to only a passage lower than the passage 10, preferably, to passage 8 or lower. Compared to the conventional subfractionation culturing method which required the culturing to a maximum passage 25 to secure a sufficient number of cells, the monoclonal stem cell may be mass-produced using only a small number of subculturing times in the improved subfractionation culturing method according to the present disclosure.

Further, when the monoclonal mesenchymal stem cells are cultured at the above-mentioned cell density, the cells have the advantage that their DNA may be less damaged, and they are less aged, thereby effectively maintaining the differentiation ability of the stem cells. Thus, the monoclonal mesenchymal stem cells may be rapidly and quickly obtained to have excellent stem cell properties.

Further, the monoclonal stem cells obtained using the method according to the present disclosure show superior atopic dermatitis prevention, amelioration or treatment effect compared to the monoclonal stem cells cultured at high density such as 4000 cells/cm$^2$.

The medium used in the present disclosure may include a medium without an antioxidant, a medium supplemented with an antioxidant, or a medium containing an antioxidant.

The medium without an antioxidant may, but be not limited to, include DMEM. If necessary, an antioxidant may further be added to the medium to perform the culture. If necessary, α-MEM containing an antioxidant may be used to perform the culture.

The antioxidants of the present disclosure may include, without limitation, antioxidants that may be used in cell cultures. They may include one or more selected from the group consisting of glutathione, cysteine, cysteamine, ubiquinol, beta-mercaptoethanol and ascorbic acid (AA). When the medium is supplemented with an antioxidant, the antioxidant may be added at a concentration of 10 to 50 μg/ml, preferably 10 to 30 μg/ml, and more preferably 25 μg/ml.

In one embodiment of the present disclosure, DMEM, more preferably LG-DMEM, is used as a medium without an antioxidant, and α-MEM is used as a medium containing ascorbic acid as an antioxidant.

Further, according to the method of the present disclosure, the monoclonal stem cells may be proliferated very effectively, thereby excluding a process of producing a working cell bank (WCB) using MCB. This results in a more simplified method compared with the conventional subfractionation culturing method in which WCB should be prepared after MCB is prepared.

The method in accordance with the present disclosure may use a medium with an antioxidant as a culture medium. The culture medium may be added with gentamicin as an antibiotic.

The mesenchymal stem cells obtained by the method in accordance with the present disclosure may finally be mesenchymal stem cells of passage 2 to less than passage 10, preferably the mesenchymal stem cells of passage 2 to passage 8, more preferably the mesenchymal stem cells of passage 2 to passage 6.

This is a lower passage number compared with the conventional process in which the results are mesenchymal stem cells obtained by at least passage 10 to passage 12, demonstrating that the cell inoculation density is controlled to easily obtain a large number of the mesenchymal stem cells rapidly proliferated in the low passage.

In accordance with the present disclosure, the monoclonal stem cell (hereinafter referred to as 'cMSC1' or 'SCM-cMSC') obtained by the improved subfractionation culturing method, that is, the subfractionation culturing method at low density lower than or equal to 2000 cells/cm$^2$, more preferably, lower than or equal to 1000 cells/cm$^2$ and at the antioxidant condition has following advantages over the monoclonal stem cell (hereinafter referred to as 'cMSC2') obtained by the conventional subfractionation culturing method: the cell size may be smaller and the cells may be more homogeneous and the cMSC1' or SCM-cMSC may reduce the thickening of dermis or epidermis having atopic dermatitis occurring therein, inhibit the production of one or more selected from the group consisting of IgE, IgG1 and IL-4, and promotes the production of INF-γ and inhibits mast cells effectively.

As used herein, "atopic dermatitis" may include congenital fever and may include, without limitation, allergic diseases of the skin having the main symptoms of dry skin and itching.

The monoclonal stem cells obtained through the method according to the present disclosure may effectively alleviate the thickening of dermis or epidermis having atopic dermatitis occurring therein and keratin symptoms that occur in skin with atopic dermatitis. In particular, the monoclonal stem cells obtained through the method according to the present disclosure may be characterized by reducing the thickening of dermis or epidermis.

Further, the monoclonal stem cell obtained through the method according to the present disclosure may improve various immune and inflammatory factors caused by atopic dermatitis. Preferably, the monoclonal stem cell obtained through the method according to the present disclosure may inhibit the production of one or more selected from the group consisting of IgE, IgG1 and IL-4, and promote the production of INF-γ.

Further, the monoclonal stem cell obtained through the method according to the present disclosure may suppress cells that cause allergic reactions, and, preferably, may be characterized by suppressing the mast cell.

The monoclonal stem cell (cMSC1 or SCM-cMSC) obtained through the method according to the present disclosure is superior to the conventional stem cell (GCM-MSC) obtained by the conventional density gradient centrifugal isolation method, as well as cMSC2 obtained by the conventional subfractionation culturing method in terms of the improvement effects of the histologic and physiological factors related to atopic dermatitis.

The pharmaceutical composition according to the present disclosure may be prepared into a formulation for administration. The pharmaceutical composition may further contain one or more pharmaceutically acceptable carrier in addition to the active ingredient. The pharmaceutically acceptable carrier contained in the pharmaceutical composition according to the present disclosure is commonly used for the formulation and may include lactose, dextrose, sucrose, sorbitol, mannitol, starch, acacia rubber, phosphoric acid calcium, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate and mineral oil, and the like, but are not limited thereto. The pharmaceutical composition according to the present disclosure may further contain lubricants, wetting agents, sweeteners, flavors, emulsifiers, suspending agents, preservatives, etc. in addition to the components as described above.

The dosage of the pharmaceutical composition according to the present disclosure may vary depending on the formulation method, administration method, administration time duration and/or administration route of the pharmaceutical composition. The dosage of the pharmaceutical composition according to the present disclosure may vary depending on several factors such as the type and extent of reaction to be achieved by administration of the pharmaceutical composition, the type of individual subject to administration, age, weight, general health, symptoms and severity of the disease, sex, diet, excretion, components of the drug or other compositions used simultaneously or in combination with transplantation of the present cells to the individual, or similar factors well known in the medical arts. One of ordinary skill in the art may readily determine and prescribe an effective dosage suitable for the desired treatment effect.

The dosage of the pharmaceutical composition according to the present disclosure may be, for example, 1 mg/kg to 1000 mg/kg per day, but the dosage does not limit the scope of the present disclosure in any way.

The administration route and administration method of the pharmaceutical composition according to the present disclosure may be independent of each other, and may not be particularly limited. Any administration route and administration method may be available as long as the pharmaceutical composition may reach a target site.

The pharmaceutical composition may be administered in an oral or parenteral administration manner. The parenteral administration includes, for example, intravenous administration, intraperitoneal administration, intramuscular administration, transdermal administration or subcutaneous administration, and includes applying, spraying or inhaling the pharmaceutical composition to a target site, but not limited to.

Furthermore, the present disclosure provides a method for preventing, treating, or ameliorating atopic dermatitis, the method including: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; 5) seeding the monoclonal stem cell in the step 4) into a culture medium at a cell density of 50 to 1000 cells/cm$^2$ and culturing the monoclonal stem cell therein, thereby obtaining the monoclonal stem cell; and 6) administering the monoclonal stem cell to an individual.

As used herein, the "individual" may include an individual who needs prevention or treatment of atopic dermatitis and may be a mammal or a mammal other than a human.

When administering the monoclonal stem cell according to the present disclosure to an individual, the monoclonal stem cell may be administered in combination with a prophylactic or therapeutic drug for atopic dermatitis as known in the art or may be administered in an formulated form together with a excipient for a stem cell-based therapeutic agent as known in the art that has been licensed or identified as harmless to the human body.

Furthermore, the present disclosure provides a stem cell for preventing, treating, or ameliorating atopic dermatitis, the stem cell being obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

Further, the present disclosure provides a cosmetic composition for prevention or ameliorating of atopic dermatitis, the composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

In addition to the stem cells according to the present disclosure, the cosmetic composition may further contain auxiliaries commonly used in the cosmetic field, such as fatty substances, organic solvents, solubilizers, thickeners and gelling agents, emollients, antioxidants, suspending agents, stabilizers, foaming agents, fragrances, surfactants, water, ionic or nonionic emulsifiers, fillers, metal ion sequestrants and chelating agents, preservatives, vitamins, blockers, wetting agents, essential oils, dyes, pigments, hydrophilic or lipophilic active agents, lipid vesicles or any other ingredients conventionally used in cosmetics.

In the cosmetic composition, the stem cell according to the present disclosure may be added in an amount of 0.01 to 15% by weight, preferably 1 to 10% by weight to a typically contained cosmetic composition.

Further, the ingredients may be introduced in amounts commonly used in the field of dermatology. In order to treat atopic dermatitis, the stem cell or its culturing solution may be diluted appropriately and applied directly to the skin. The pharmaceutical composition for the treatment of skin diseases according to the present disclosure may be prepared as ointments to be effectively applied to the affected area. The ointment may be prepared by mixing the pharmaceutical composition for treating atopic dermatitis according to the present disclosure with an inorganic substance and then coating the mixture with a fat-soluble base. The inorganic material may include a material excellent in antibacterial, anti-inflammatory effect, epidermis regeneration effect, and specific examples thereof include zinc oxide, zinc carbonate, iron oxide. Further, it is desirable to further use a ceramic carrier in which the pharmaceutical composition for treating atopic dermatitis according to the present disclosure as a water-soluble substance may be safely impregnated. As the ceramic carrier, zeolite, talc, gypsum, seed powder and mixtures thereof are preferably used. Such a ceramic carrier is excellent in the impregnation of the water-soluble component therein to facilitate the supply of the water-soluble component to the skin.

Further, the present disclosure provides a quasi-drug composition for prevention or ameliorating of atopic dermatitis, the composition containing a monoclonal stem cell obtained via: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein.

The term "quasi-drug" as used herein means any one of the following commodities: fibers, rubber products or similar products used for the purpose of treatment, alleviation, medical care, or prevention of human or animal diseases; non-appliance, non-machinery or similar commodities that have insignificant influences on or do not directly act upon human bodies; preparations used for sterilization, insecticide, and uses similar thereto for the purpose of preventing infectious diseases, and means products used for the purposes of diagnosis, medical care, alleviation, treatment, or prevention of diseases of human beings or animals, excluding appliances, machinery and equipment; and products, other than appliances, machinery or equipment, used for the purpose of exerting pharmacological effects upon the structure or functions of human beings or animals, in particular, preparations for external application to the skin or personal hygiene products, but the present disclosure is not limited thereto.

In the case where the composition of the present disclosure is included in the quasi-drug for prevention or ameliorating of atopic dermatitis, the composition may be used as it is or may be used together with other quasi-drug ingredients and may be properly used according to a general method. A mixed amount of active ingredients may be suitably determined according to a use purpose. The quasi-drug of the present disclosure is not particularly limited thereto but may be prepared and used in a form of for example, creams, lotions, aerosols, shampoos, gels or packs. In the case of the creams, lotions, aerosols, shampoos, gels or packs, base materials such as white petrolatum, yellow petrolatum, lanolin, bleached beeswax, cetanol, stearyl alcohol, stearic acid, hydrogenated oil, gelling hydrocarbon, polyethylene glycol, liquid paraffin, and squalane; solvents and dissolution aids such as oleic acid, myristic acid isopropyl, triisooctanoic acid glycerin, crotamiton, diethyl sebacate, diisopropyl adipate, hexyl laurate, fatty acid, fatty acid ester, aliphatic alcohol and vegetable oil; antioxidants such as tocopherol derivatives, L-ascorbic acid, dibutylhydroxytoluene, and butylhydroxyanisole; preservatives such as parahydroxybenzoic acid ester; humectants such as glycerin, propylene glycol and sodium hyaluronate; surfactants such as polyoxyethylene derivatives, glycerin fatty acid esters, sucrose fatty acid esters, sorbitan fatty acid esters, propylene glycol fatty acid esters, and lecithin; thickening agents such as carboxyvinyl polymer, xanthan gum, carboxymethylcellulose, carboxymethylcellulose sodium salts, hydroxypropylcellulose, hydroxypropylmethylcellulose, and the like are included.

In the case of an aerosol agent, base materials such as white petrolatum, yellow petrolatum, lanolin, bleached beeswax, cetanol, stearyl alcohol, stearic acid, hydrogenated oil, gelling hydrocarbon, polyethylene glycol, liquid paraffin, and squalane; solvents and dissolution aids such as oleic acid, myristic acid isopropyl, diisopropyl adipate, isopropyl sebacate, triisooctanoic acid glycerin, crotamiton, diethyl sebacate, hexyl laurate, fatty acid, fatty acid ester, aliphatic alcohol and vegetable oil; antioxidants such as tocopherol derivatives, L-ascorbic acid, dibutylhydroxytoluene, and butylhydroxyanisole; preservatives such as parahydroxybenzoic acid ester; humectants such as glycerin, propylene glycol and sodium hyaluronate; surfactants such as polyoxyethylene derivatives, glycerin fatty acid esters, sucrose fatty acid esters, sorbitan fatty acid esters, propylene glycol fatty acid esters, and lecithin; thickening agents such as carboxyvinyl polymer, xanthan gum, carboxymethylcellulose, carboxymethylcellulose sodium salts, hydroxypropylcellulose, hydroxypropylmethylcellulose, which are used in the preparation of ointments, creams, gels, suspensions, emulsions, solutions and lotions; additionally, various stabilizers, buffers, mating agents, suspensions, emulsifiers, fragrances, preservatives, subsolubilizers, and other suitable additives may be mixed. Further, if necessary, stabilizers, preservatives, absorption promoters, pH adjusters, and other suitable additives may be mixed.

Furthermore, the present disclosure provides a method for preparing a composition for prevention, treatment, or ameliorating of atopic dermatitis, the method including: 1) culturing bone marrow isolated from an individual in a first vessel; 2) transferring only first supernatant in the first vessel to a second vessel and culturing the first supernatant in the second vessel; 3) culturing cells in the second vessel and obtaining second supernatant in the second vessel; 4) sequentially repeating the steps 2) and 3) at least one time while the first supernatant in the step 2) is replaced with the second supernatant in the step 3), thereby obtaining a monoclonal stem cell; and 5) seeding the monoclonal stem cell in the step 4) into a culture medium at a cell density of 50 to 1000 cells/cm$^2$ and culturing the monoclonal stem cell therein, thereby obtaining a monoclonal stem cell.

According to the present disclosure, the monoclonal stem cells may be obtained quickly and easily without WCB preparation, which exhibits superior atopic dermatitis prevention, amelioration or treatment effects compared to the monoclonal stem cells obtained by the conventional subfractionation culturing methods. The composition may include, without limitation, pharmaceutical, food, quasi-drugs, and cosmetic compositions.

In the preparation method according to the present disclosure, 5) seeding the monoclonal stem cell includes seeding the monoclonal stem cell into the culture medium at a cell density of 1000 cells/cm$^2$.

Further, in the preparation method according to the present disclosure, the medium of step 5) may contain the antioxidant added thereto.

In the treatment method and preparation method according to the present disclosure, the contents as described above with reference to the composition may be equally applied. Duplicate content is omitted to avoid complexity of the description.

Hereinafter, the present disclosure is described in detail with accompanying Examples.

The following Examples are only intended to illustrate the present disclosure but do not limit to the contents of the present disclosure.

Example 1. Establishment of Improved Subfractionation Culturing Method

In order to prepare monoclonal mesenchymal stem cells with excellent effect on atopic dermatitis, the improved mesenchymal stem cell subfractionation culturing method and proliferation method were used. In the improved mesenchymal stem cell subfractionation culturing method and proliferation method, the cell density and culturing medium among the culturing conditions of the subfractionation culturing method as described in Korean Patent Application No. 10-2006-0075676 may vary. In the experiments below, the cell culturing densities of monoclonal mesenchymal stem cells (cMSC) obtained through the subfractionation culturing method vary to 50 cells/cm$^2$ (low density), 1000 cells/cm$^2$ (medium density) and 4000 cells/cm$^2$ (high density), thereby analyzing the characteristics of the cells.

1.1 Identification of Morphological Changes of Mesenchymal Stem Cells (MSCs) According to Cell Density First, the experiments were conducted to identify the morphological changes of MSCs according to cell density in long-term culture. The MSCs having passage 5 (P5), passage 10 (P10) and passage 15 (P15) were used for the long-term culture conditions. The MSCs were inoculated in LG-DMEM medium under the condition of low density, medium density and high density, respectively. Thereafter, the morphological changes of the cells were observed through a microscope to determine whether or not the stem cells were aged. The results are illustrated in FIG. 2.

Figure 2:
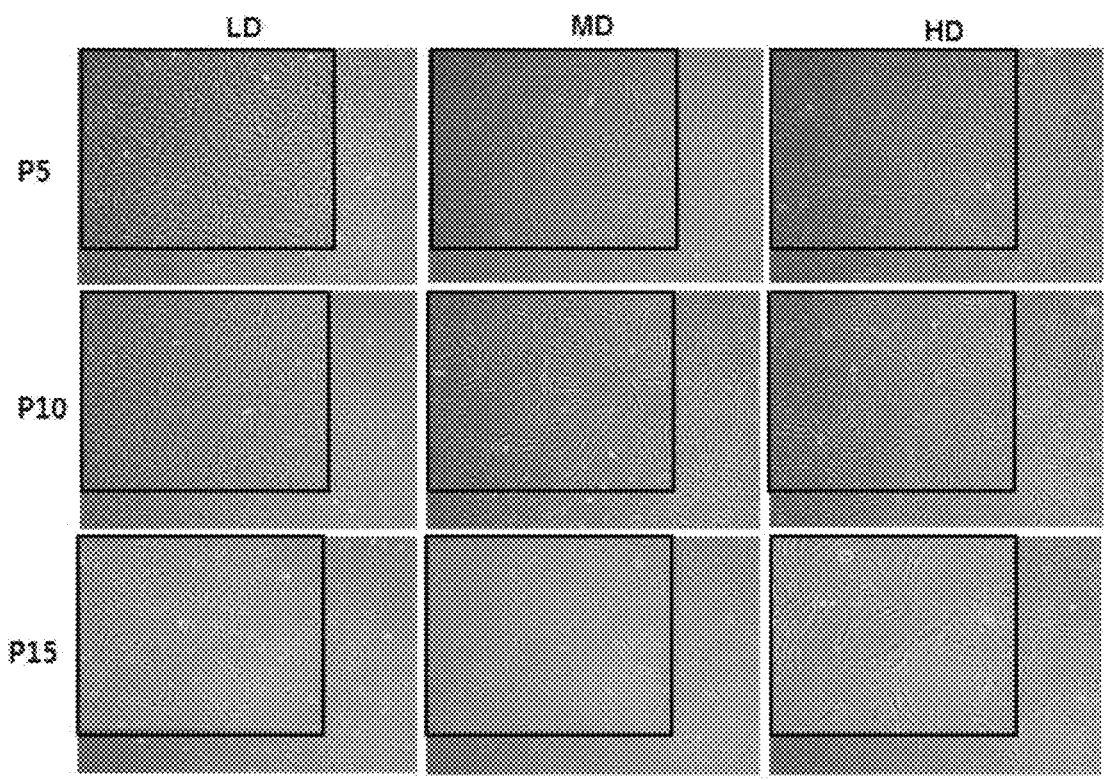
FIG. 2 illustrates the results obtained by a microscope for the morphological changes of monoclonal mesenchymal stem cells according to cell culture density and cell culture passage.

As illustrated in FIG. 2, the cell size and morphological pattern of P5 and P10 were different according to the cell density. In particular, P15 cultured under a high density culture condition had flat and enlarged MSCs. This morphology form indicates the typical aging of MSCs, which confirms that the cell density is controlled in the long-term culture, resulting in the control of MSC's aging.

1.2 Identification of MSC Size and Granularity According to Cell Density

In order to further identify the change of stem cells according to the cell density, the cell size and granularity, which were known to be increased in aged cells, were analyzed by FACS analysis. Thus, the results are illustrated in FIG. 3.

Figure 3A:
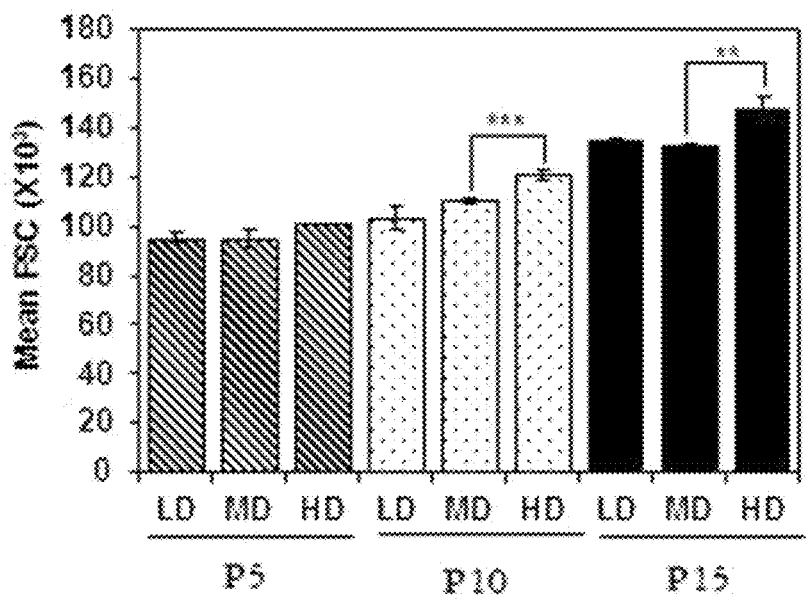
FIG. 3A illustrates the results of FACS (flow cytometry) analysis of changes in the cell size and granularity of monoclonal mesenchymal stem cells based on a mean FSC (forward scatter) light according to cell culture density and cell culture passage ($*p<0.05$, $p<0.01$ and $*p<0.005$).
Figure 3B:
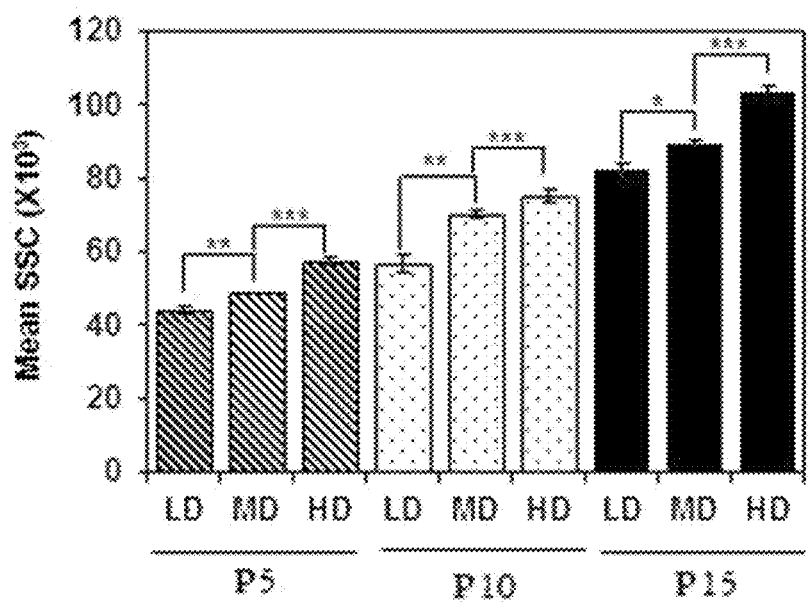
FIG. 3B illustrates the results of FACS analysis of changes in the cell size and granularity of monoclonal mesenchymal stem cells based on a mean SSC (side scatter) light according to cell culture density and cell culture passage ($*p<0.05$, $p<0.01$ and $*p<0.005$).

As illustrated in FIG. 3, the cell size did not show a significant difference at P5, but P10 and P15 showed significant differences according to the cell density. In particular, the cell sizes in P10 and P15 were significantly increased under a culture condition of the high cell density, thereby further promoting aging of cells. Similarly, the cell granularity also was significantly increased as the cell density was increased in all passages. Therefore, controlling cell density of MSC in long-term culture may be a factor to control aging of cells. Further, the cell culture density is lower to improve the morphological changes in the late passage.

1.3 Identification of Aging of MSC According to Cultured Cell Density

The beta-gal-staining analysis was performed to identify whether the morphological changes confirmed in Examples 1.1 and 1.2 were actually an age-dependent phenomenon of MSC, which may selectively stain aging cells, and RT-PCR was carried out to compare the expression of aging-related genes P15, P16 and PCNA gene, a proliferation marker. The results are illustrated in FIGS. 4 and 5, respectively.

Figure 4:
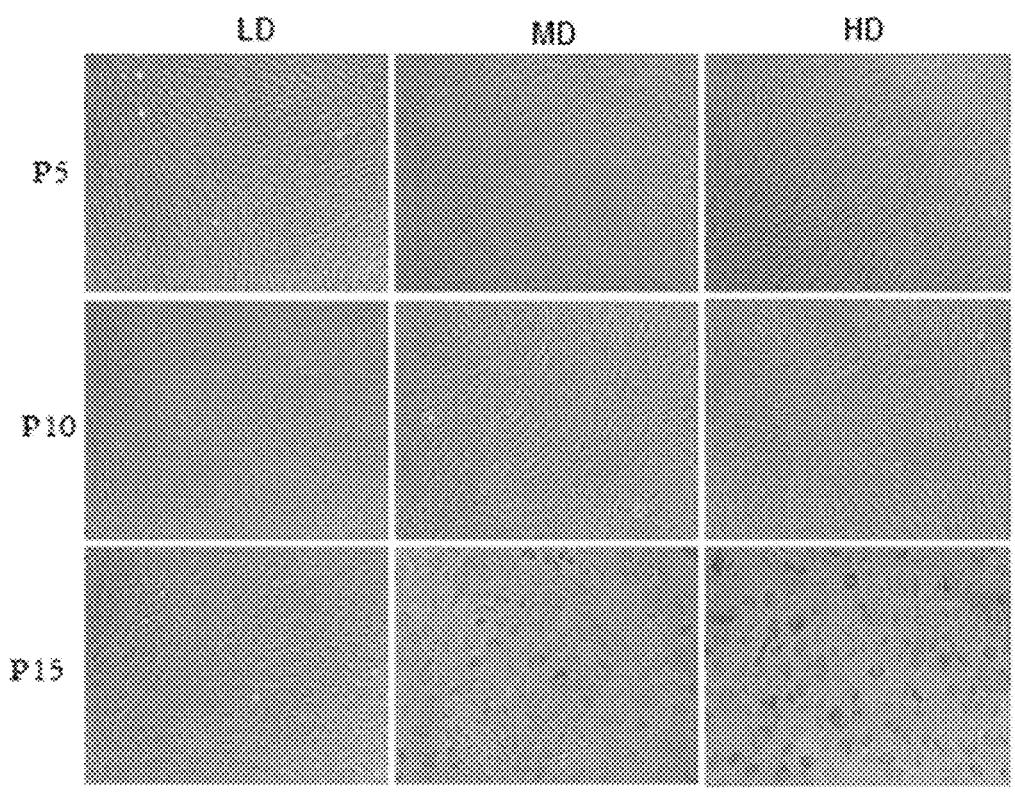
FIG. 4 illustrates the results of identifying whether cells are aged based on beta galactosidase (beta gal) activity via staining monoclonal mesenchymal stem cells in which cell culture densities and cell culture passages varies.
Figure 5:
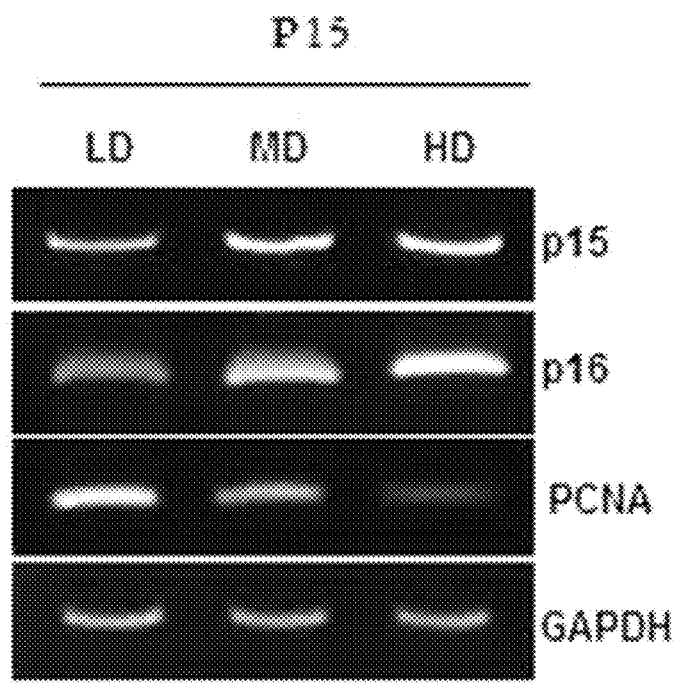
FIG. 5 illustrates the results of RT-PCR of P15 and P16 as aging-related genes and PCNA as a proliferation marker after culturing monoclonal mesenchymal stem cells of passage 15 (P15) while the cell culture density varies.

As illustrated in FIG. 4, passage 5 (P5) and passage 10 (P10) did not have the staining of aged cells at all cell densities, but passage 15 (P15) had the staining of aged cells markedly increased as the cell density increased. As illustrated in FIG. 5, in passage 15 (P15), gene expression of CDK inhibitors P15 and P16, which are genes related to aging, was increased as the cell density increased, and PCNA, which is a proliferation marker, decreased.

These results demonstrate that the morphological changes of MSCs are related to the aging of MSCs and that the manipulation of the cell culture density in the subculture may control the aging of MSCs.

1.4 Identification of Change of Proliferation Ability of MSCs According to Culture Cell Density It is known that the proliferation ability of MSCs progressively decreases as cells are subcultured and aged. Therefore, the proliferation ability may be used as a criterion for identifying the aging of MSCs. Thus, the proliferation ability of MSCs according to the cell culture density was compared during long-term cell culture. The proliferation ability of each cell was determined by calculating the proliferation rate according to each passage using the number of cells which were initially inoculated and the number of cells which were obtained after the culture. The results are shown in Table 1 and FIG. 6.

TABLE 1

| (cell/cm$^2$) | Fold Increase | | |
|---|---|---|---|
| | P5 | P10 | P15 |
| 50 | 88.4 ± 6.5 | 34.3 ± 5.0 | 16.4 ± 1.3 |
| 1000 | 8.5 ± 0.3 | 4.9 ± 0.5 | 3.1 ± 0.4 |
| 4000 | 3.0 ± 0.1 | 1.9 ± 0.1 | 1.1 ± 0.1 |

Figure 6:
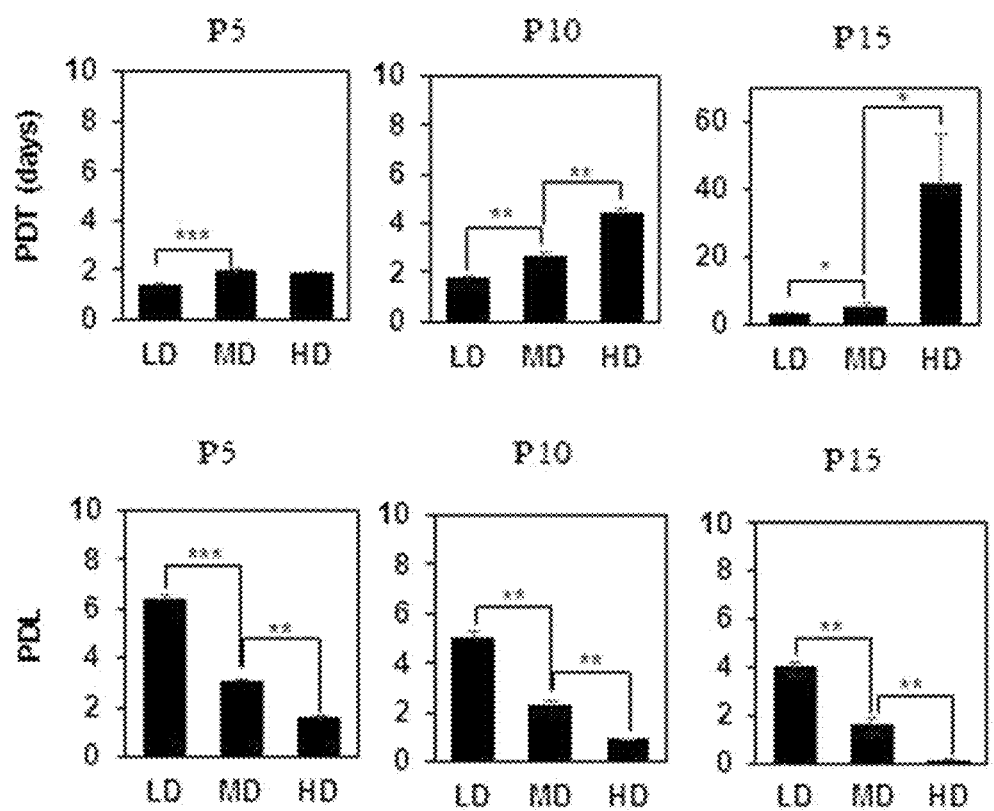
FIG. 6 illustrates the results of identifying the proliferation ability of monoclonal mesenchymal stem cells based on population doubling time (PDT) and population doubling level (PDL) according to cell culture density and cell culture passage ($*p<0.05$, $p<0.01$ and $*p<0.005$).
Figure 7A:
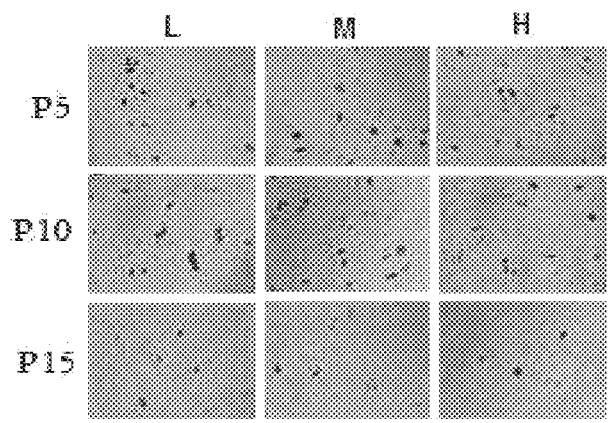
FIGS. 7A-7D illustrate the results of identifying the differentiation capacity of monoclonal mesenchymal stem cells according to cell culture density and cell culture passage ($*p<0.05$, $p<0.01$ and $*p<0.005$)
Figure 7B:
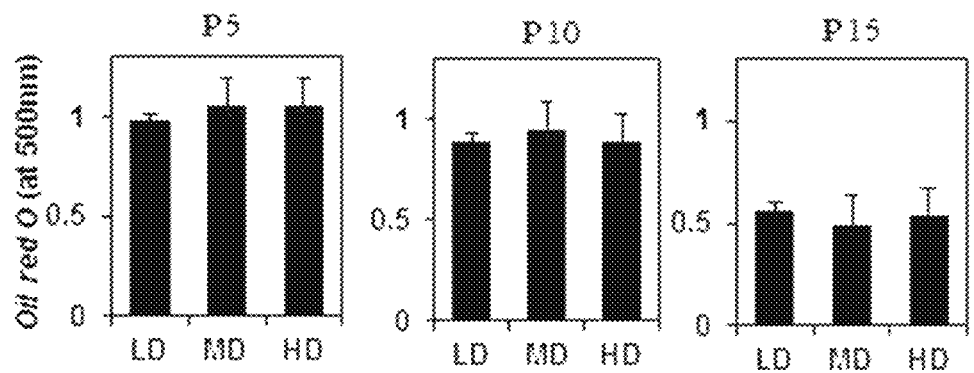
Figure 7C:
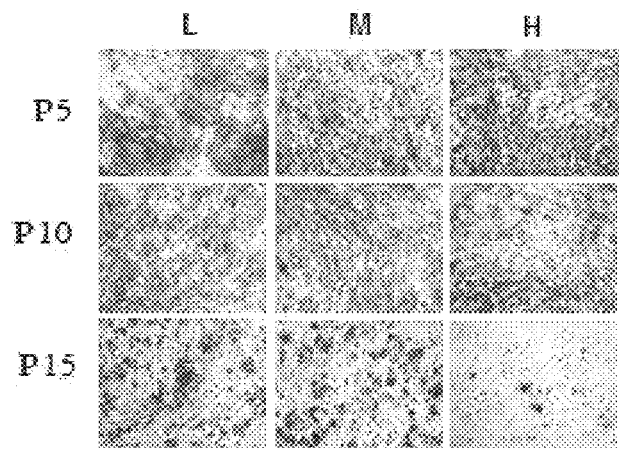
Figure 7D:
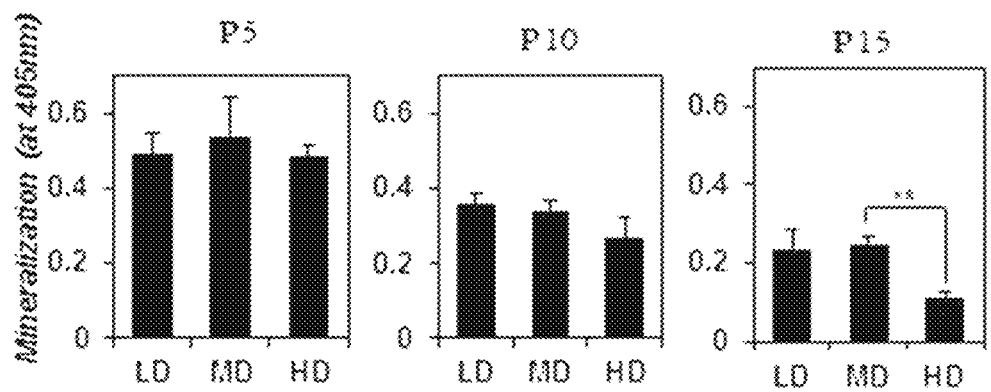

As shown in Table 1, the fold increases were 88.4, 34.3 and 16.4 at passage 5 (P5), passage 10 (P10) and passage 15 (P15), respectively, in MSCs cultured at a low density. Meanwhile, the fold increases in MSCs cultured at a medium density were 8.5, 4.9 and 3.1 at P5, P10 and P15, respectively. Further, the fold increases were 3.0, 1.9, and 1.1 at P5, P10 and P15, respectively, in MSCs cultured at a high density. As illustrated in FIG. 6, the PDT and the PDL also have the same pattern as the fold increase. These results indicate that the proliferation ability of MSCs may be maintained by lowering the cell density in long-term MSC culture and that even though performing the same subculture, the aging of MSCs may be inhibited and the lifespan of MSCs may be prolonged.

1.5 Identification of Change of Differentiation Potential of MSCs According to Culture Cell Density The differentiation potentials according to P5 to P15 cultures were compared to identify whether culture cell density affects the ability of stem cells. The ability of stem cells to differentiate into adipocytes and osteocytes was confirmed. Qualitative and quantitative analyzes were carried out at each passage and density. Specifically, NCS (Newborn Calf Serum) (Gibco), $10^{-7}$ mol dexamethasone (Sigma), 0.5 mM IBMX (Sigma), 10 µg/ml insulin (Sigma), and 100 µm indomethacin (Sigma) were added to a high glucose DMEM culture medium to prepare the adipocyte differentiation medium, and then the experiment was carried out. After 7 days of differentiation, it was confirmed by Oil red O histochemical staining. After the Oil red O histochemical staining, it was eluted with isopropyl alcohol and measured at 500 nm and quantitatively analyzed.

The osteoclast differentiation medium was prepared and used by adding FBS (Gibco), 50 µg/ml ascorbic 2-phosphate (Sigma), $10^{-8}$ mol dexamethasone (Sigma) and 10 mM β-glycerophosphate (Sigma) to α-MEM medium. After 21 days of differentiation, it was confirmed by Alizarin red S histochemical staining. Further, after Alizarin red S histochemical staining, it was eluted with 10% acetic acid, measured at 405 nm and quantitatively analyzed. The adipocyte differentiation ability and the osteoclast differentiation ability were confirmed as described above. The results are illustrated in FIG. 7.

As illustrated in FIG. 7, the adipocyte differentiation potential decreased overall as the passage progressed, but the difference according to the density was not apparent. On the other hand, the osteoclast differentiation potential significantly decreased in the passage 15 (P15) culture group under the condition of high density. These results show that the osteoclast differentiation potential of MSCs may be maintained better when culturing at a low cell density.

1.6 Antigen Profile Analysis of MSCs According to Culture Cell Density

Experiments were carried out to identify whether or not the cell culture density also affects the stem cell antigen expression. Flow cytometry was performed to identify the changes in positive and negative antigen expression according to each passage and culture density. The results are shown in Table 2.

TABLE 2

|  |  | Passage | | | | | | | | |
| --- | --- | --- | --- | --- | --- | --- | --- | --- | --- | --- |
|  |  | P5 | | | P10 | | | P15 | | |
| | Density | LD | MD | HD | LD | MD | HD | LD | MD | HD |
| positive marker | CD29 | 100 | 99.9 | 99.7 | 90 | 99.6 | 99.5 | 87.3 | 97.8 | 48.5 |
| | CD44 | 99.9 | 99.9 | 100 | 99.4 | 99.7 | 99.6 | 93.8 | 80.6 | 31.4 |
| | CD73 | 100 | 100 | 99.8 | 98.7 | 99.6 | 99.6 | 60.3 | 20.8 | 3.8 |
| | CD90 | 99.9 | 100 | 100 | 99.5 | 99.9 | 99.8 | 94.9 | 98.5 | 65 |
| | CD105 | 100 | 100 | 99.8 | 99.3 | 99.7 | 99.8 | 15.7 | 3.65 | 4.4 |
| Negative marker | CD31 | 2.73 | 3.76 | 4.04 | 1.63 | 3.8 | 3.93 | 1.57 | 2.69 | 3.19 |
| | CD104 | 2.19 | 3.55 | 4.06 | 1.52 | 4.57 | 4.22 | 2.63 | 3.62 | 2.12 |
| | HLA-DR | 2.82 | 3.04 | 3.62 | 2.42 | 4.47 | 3.97 | 2.1 | 3.44 | 2.76 |
| | CD14 | 3.19 | 3.95 | 4.04 | 3.26 | 5.81 | 4.24 | 2.38 | 3.07 | 2.93 |

As shown in Table 2, the change of the expression of the negative marker was not clearly apparent, but the expression level of some positive markers was changed according to the cell culture density even in the same passage.

In particular, when cells were cultured at a high density in passage 15 (P15), the expression level of most positive markers was significantly decreased. Further, CD73 and CD105 showed negative expression. Thus, cell culturing with a low cell density may be a critical factor.

1.7 Comparison of ROS Production and DNA Damage According to Culture Cell Density It is known that the decrease of mesenchymal stem cell function is associated with DNA damage. In particular, DNA damage induced by ROS, which is an active oxygen species, is known to promote aging of MSCs. Therefore, in order to identify whether or not total ROS production and DNA damage caused thereby are different, fluorescence intensity analysis was performed to compare the total amount of cellular ROS according to passage and cell culture density. Comet analysis was performed to identify the degree of DNA damage. The results are illustrated in FIG. 8.

Figure 8A:
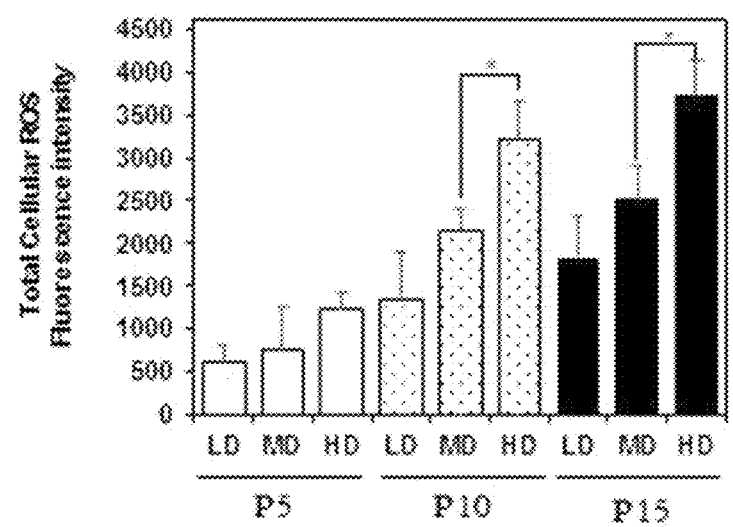
FIG. 8A is a view illustrating total ROS (reactive oxygen species) production of monoclonal mesenchymal stem cells according to cell culture density and cell culture passage.
Figure 8B:
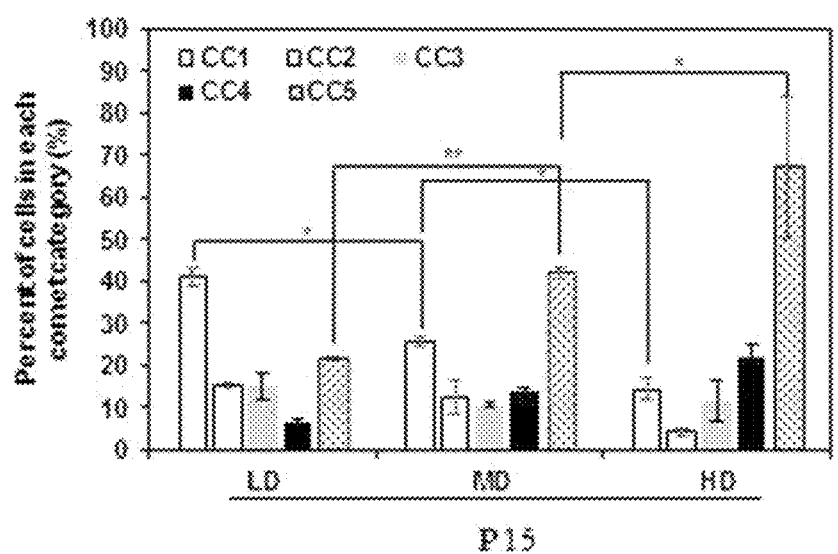
FIG. 8B is a view illustrating the results of comet assay on DNA damage caused by total ROS production according to cell culture density and cell culture passage ($*p<0.05$, $p<0.01$ and $*p<0.005$).

As illustrated in FIG. 8, total ROS production tended to increase as the cell culture density increased in all passages. In particular, ROS production significantly increased at passage 10 (P10) and passage 15 (P15) (See FIG. 8A). In the comet analysis, the data were classified from CC1 with the weakest DNA damage to CC5 with the most severe DNA damage. The CC5 with the most severe DNA damage exhibited a significant increase as the cell culture density increased. On the other hand, the CC1 tended to decrease significantly as the cell density increased (See FIG. 8B).

Further, in order to identify whether or not ROS caused DNA damage, an experiment was conducted to identify the concentration of 8-OHdG which may identify DNA damage caused by ROS. The analysis of 8-OHdG is as follows. 50 μl the DNA sample collected from each cell was placed on an 8-OHdG conjugate coated plate and incubated at room temperature for 10 minutes. Then, an anti-8-OHdG antibody was added thereto and the mixture was incubated at room temperature for 1 hour. After washing three times, secondary antibody-enzyme conjugate was added to each well, and the mixture was incubated at room temperature for another 1 hour. After washing three times, a substrate solution was added thereto, and the mixture was incubated at room temperature for 30 minutes. Finally, a stop solution was added thereto. The absorbance intensity thereof was measured at 450 nm. The results are illustrated in FIG. 9.

Figure 9:
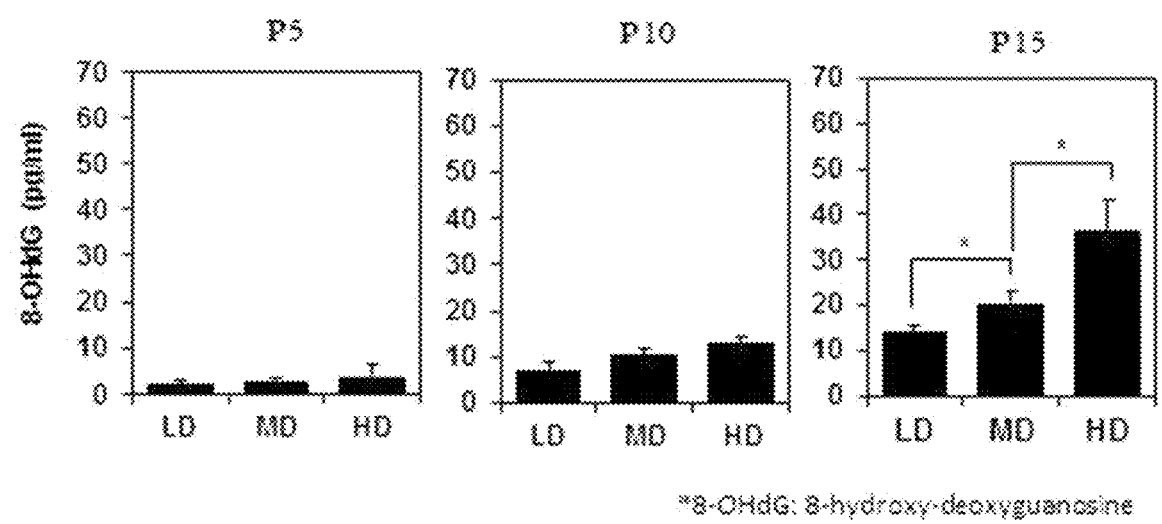
FIG. 9 is a view illustrating the results of measuring 8-OHdG (8-hydroxy-2'-deoxyguanosine) concentration in order to identify the degree of DNA damage by ROS produced according to cell culture density and cell culture passage ($*p<0.05$, $p<0.01$ and $*p<0.005$).

As illustrated in FIG. 9, as the cell culture density increased, the concentration of 8-OHdG was significantly increased in passage 15 (P15) group in which DNA damage was most severe. These results demonstrate that ROS produced under the culture condition of the high density caused DNA damage to increase, thereby promoting aging of MSCs.

These results show that lowering the cell culture density may play a role in protecting MSCs from DNA damage which is caused by increased ROS production of MSCs.

1.8 Identification of MSC Proliferation and ROS Production Ability According to Antioxidant Treatment In order to identify whether or not ROS produced under the culture condition of high density affects the proliferation of MSCs, an experiment for eliminating ROS was performed. 25 μl/ml ascorbic acid, an antioxidant, was added to the culture medium under the culture condition of high density in passage 11 (P11) to passage 15 (P15). Then, the fold increase of proliferation was compared between the two groups. The results are illustrated in FIG. 10.

As illustrated in FIG. 10, the fold increase was 2.6, 1.9, and 1.6 at P11 to P15 in the high density culture condition. As passage number increased, the proliferation ability decreased, and as a result, aging began. However, treating with the antioxidant induced to maintain high proliferation ability at about 50% in all passages. In the antioxidant treated group, the growth fold increase was 3.8, 2.9 and 2.5 in P11 to P15, respectively. The proliferation ability was maintained high even at P15.

At the endpoint P15, ROS levels were confirmed between the high density culture condition alone and high density culture condition+antioxidant treated group. The results are illustrated in FIG. 11.

Figure 11:
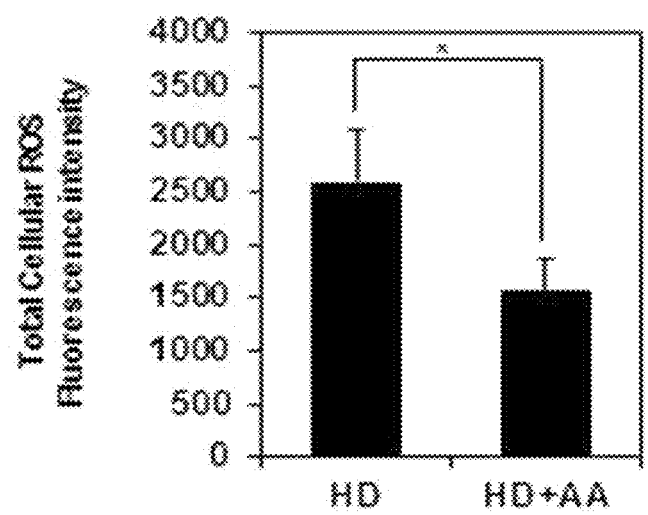
FIG. 11 illustrates the results of comparing levels of ROS produced by culturing the monoclonal mesenchymal stem cells of passages 11 to 15 under the condition of only high density (HD) and high density+ascorbic acid addition (HD+AA) ($*p<0.05$, $p<0.01$ and $*p<0.005$).

As illustrated in FIG. 11, the ROS level also decreased under the condition that proliferation was increased by treating ascorbic acid, an antioxidant. Therefore, MSC culture was preferably performed at a low cell density rather than a high density. ROS production induced by a high density of cell culture was eradicated with an antioxidant, thereby resulting in an increase of MSC proliferation ability. In other words, ROS at a high density inhibited MSC proliferation ability. As the cell density was lower, the ROS production was decreased, and the MSC proliferation ability was promoted.

In conclusion, these results indicate that controlling the cell density at the density of 1000 cells/cm$^2$ or less in culture conditions is important to maintain the proliferation, culture and stem cell ability of the monoclonal mesenchymal stem cells obtained through the subfractionation culturing method. Culture with an antioxidant inhibits oxidative stress induced by cell culture, thereby promoting MSC proliferation efficiently. Further, when comparing culturing conditions with the low cell densities, stem cells of a passage higher than or equal to the passage 10, such as P15 were more prominent in morphological changes and had the promoted stem cell aging and decreased differentiation ability compared to stem cells of a passage lower than the passage 10, such as passage 5. Thus, it was identified that the culturing at the low passage number lower than the passage 10 and at a density of 1000 cells/cm$^2$ or less was most effective.

Example 2. Verification of Improved Subfractionation Culturing Method

Example 1 has confirmed that the control of the cell density and the passage, and the addition of the antioxidant may be critical factors in the MSC culture obtained by the subfractionation culturing method. Therefore, the experiments were conducted to analyze the proliferation ability of single colony MSCs and their effect of obtaining cells while varying the cell culture density of monoclonal mesenchymal stem cells obtained by the conventional method, that is, the subfractionation culturing method described in Korean Patent Application No. 10-2006-0075676, and using a culture medium containing ascorbic acid (AA) as an antioxidant.

Example 1 of Korean Patent Application No. 10-2006-0075676 as previously disclosed, described a method for isolating mesenchymal stem cells from bone marrow and culturing the mesenchymal stem cells via a subfractionation culturing method as shown in FIG. 1, and disclosed that colonies as the monoclonal cell groups as obtained via the subfractionation culturing method were transferred to culture vessel at 100 to 600 cells per well.

Further, Korean Patent Application No. 10-2014-0170045 discloses a method for isolating and culturing bone marrow-derived mesenchymal stem cells using a subfractionation culturing method and discloses the fact that the colonies are plated at 50 to 100 cells/cm$^2$.

However, Korean Patent Application Nos. 10-2006-0075676 and 10-2014-0170045 disclose a configuration in which colonies as the monoclonal cell groups as obtained by the subfractionation culturing method are counted and are transferred to 6-well plates and are plated at the low concentration to expand the cells for seed cell preparation for subculturing, that is, disclose the condition of the culturing of the colony corresponding to passage 1. However, Korean Patent Application Nos. 10-2006-0075676 and 10-2014-0170045 fail to disclose the configuration on cell density control in repetitive culturing of individual cells other than colonies subsequent to passage 2, and the effect thereof. According to the conventional subfractionation culturing method as described in the above Korean Patent Application Nos. 10-2006-0075676 and 10-2014-0170045, culturing of a passage higher than or equal to passage 10 should be performed to obtain the monoclonal stem cells at an amount sufficient for the prevention, treatment and improvement of atopic dermatitis. However, in the improved subfractionation culturing method in accordance with the present disclosure, large quantities of the monoclonal stem cells may be obtained effectively under low cell density conditions at the passage lower than or equal to a passage 8 as subsequent to the passage 2.

Specifically, in this improved method, after culturing the colonies of passage 1 (P1) obtained through the subfractionation culturing method, the cells were dispensed at a lower density of 1000 cells/cm$^2$ or less in the subculture after passage 2 (P2). An effect thereof was compared with the effect of the culturing at the cell density of 4000 cells/cm$^2$. Further, different cell culturing mediums, that is, α-MEM medium containing antioxidant and LG-DMEM medium without antioxidant are used, and the cell proliferation effects thereof were compared with each other.

Experimental groups for identifying the effect of the improved subfractionation culturing method are shown in Table 3. The improved processes of the improved subfractionation culturing method over the conventional subfractionation culturing are schematically illustrated in FIG. 12A and FIG. 12B.

Figure 12A:
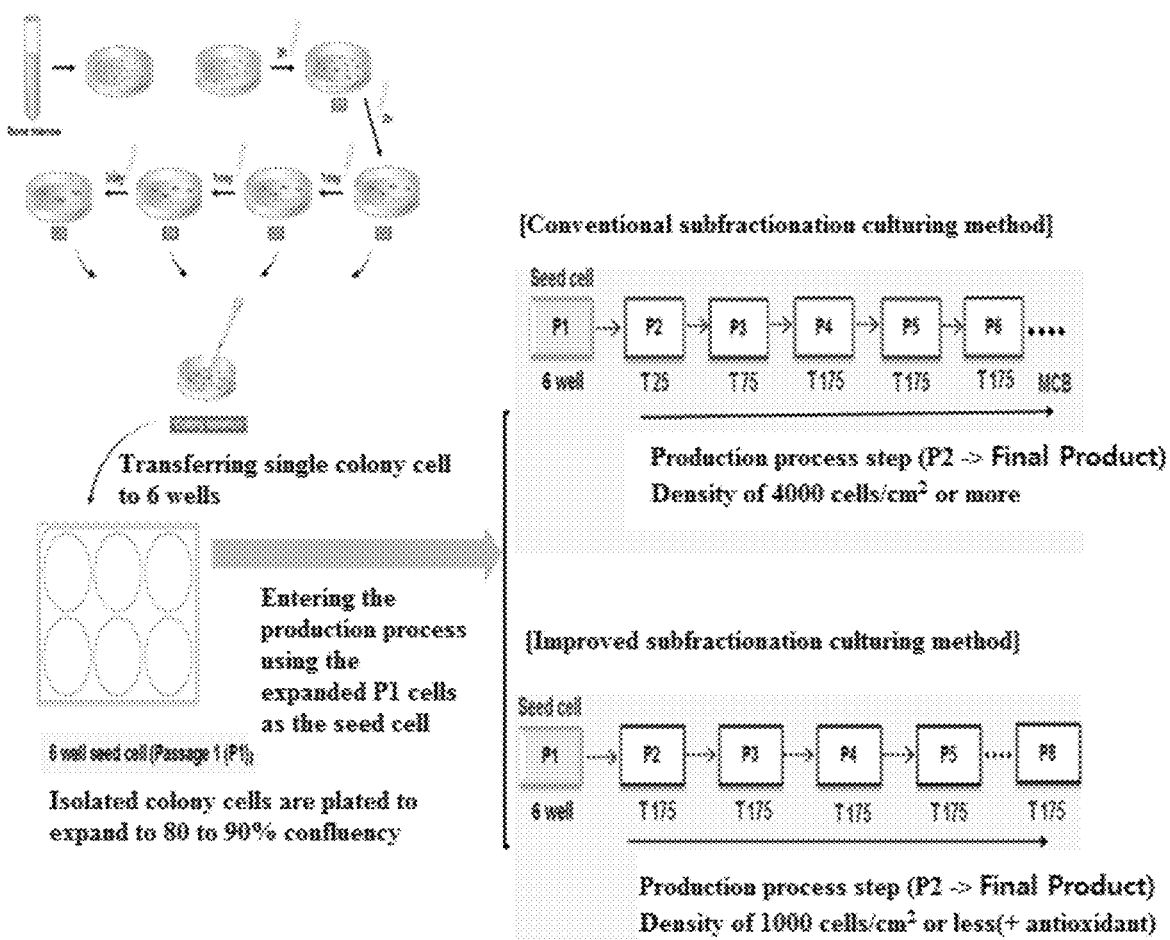
FIG. 12A shows a comparison between a conventional subfractionation culturing method and an improved subfractionation culturing method.
Figure 12B:
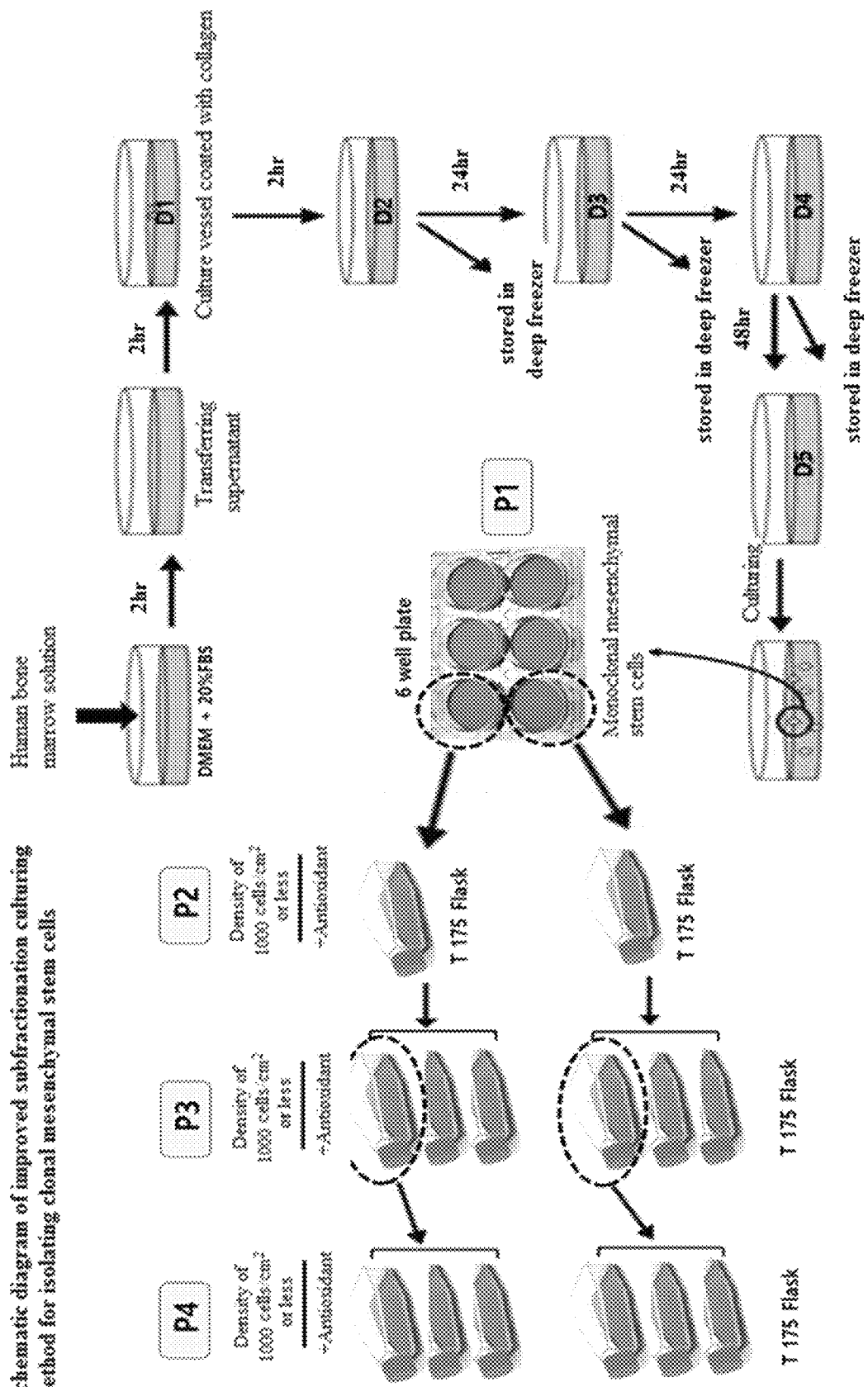
FIG. 12B is a schematic diagram of an improved subfractionation culturing method and shows a low-density culturing subsequent to passage 2 as different from the conventional subfractionation culturing method.
Figure 13:
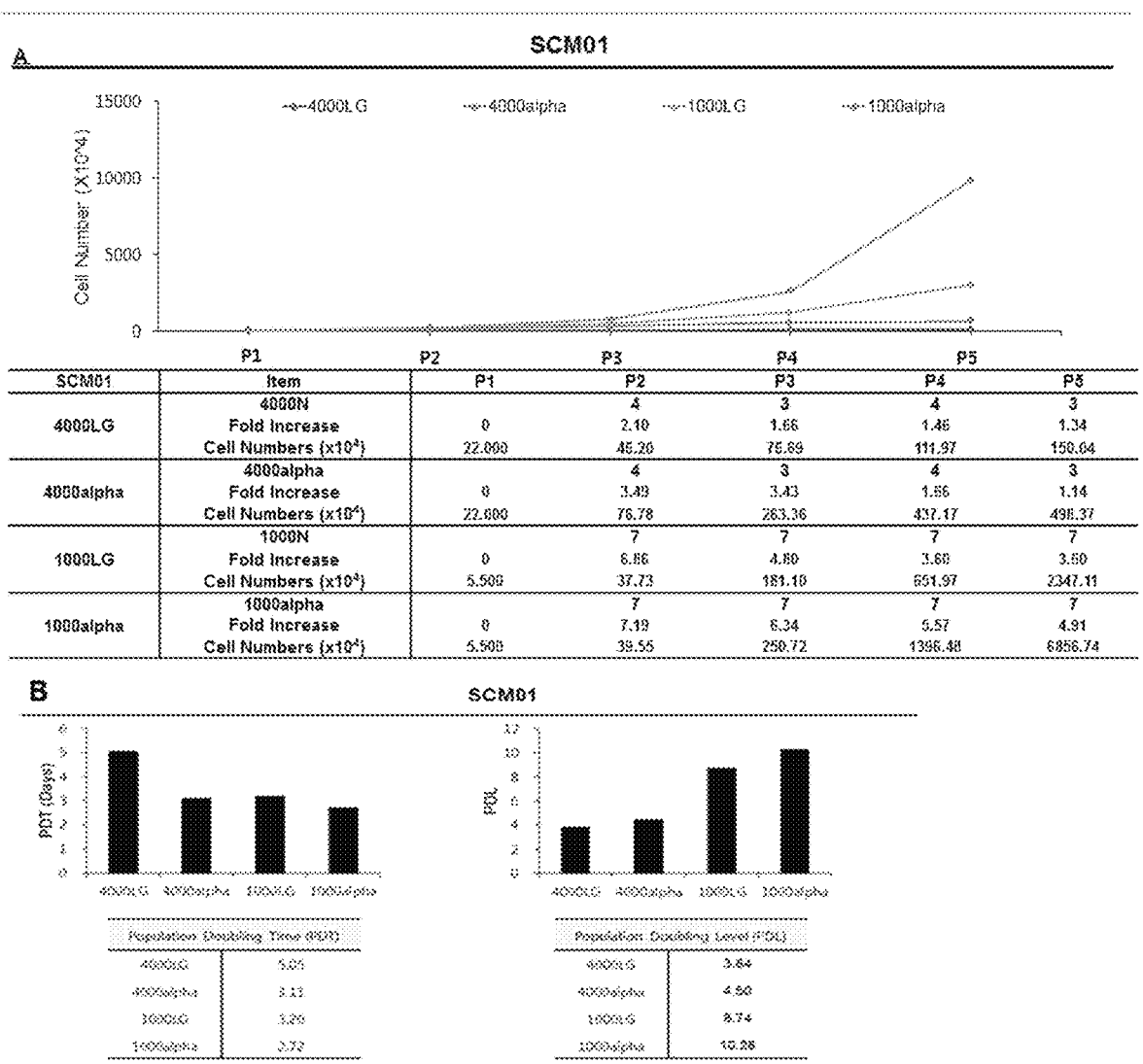
FIGS. 13-20 illustrate the results of identifying proliferation rate of cells in which SCM01 to SCM08 monoclonal mesenchymal stem cells obtained by the subfractionation culturing method are inoculated at the density of 1000 or 4000 cells/cm$^2$, and the cells are cultured using LG-DMEM (Dulbecco's Modified Eagle Medium, low glucose) culture medium and α-MEM (Minimum Essential Medium α) culture medium with or without an antioxidant; A of each of FIG. 13 to FIG. 20 illustrates changes in cell numbers according to passage 1 (P1) to passage 5 (P5) of each of experimental groups; B of each of FIG. 13 to FIG. 20 illustrates the results of PDT and PDL of each of experimental groups.
Figure 14:
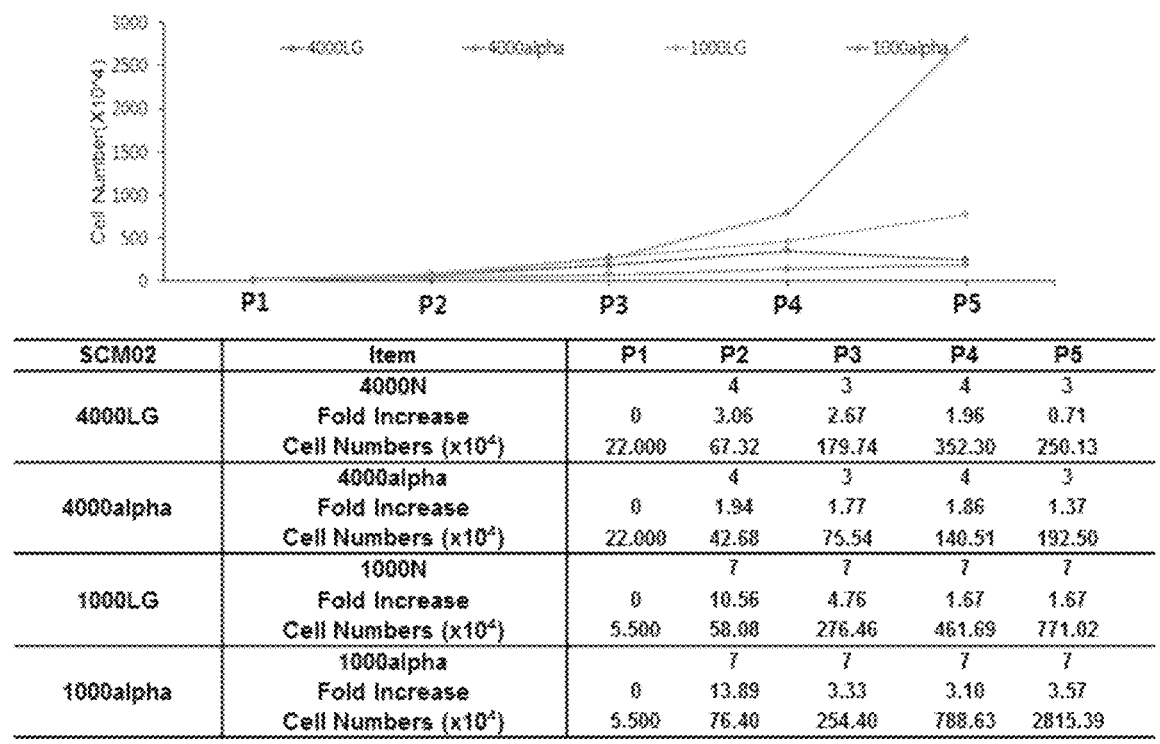
Figure 14:
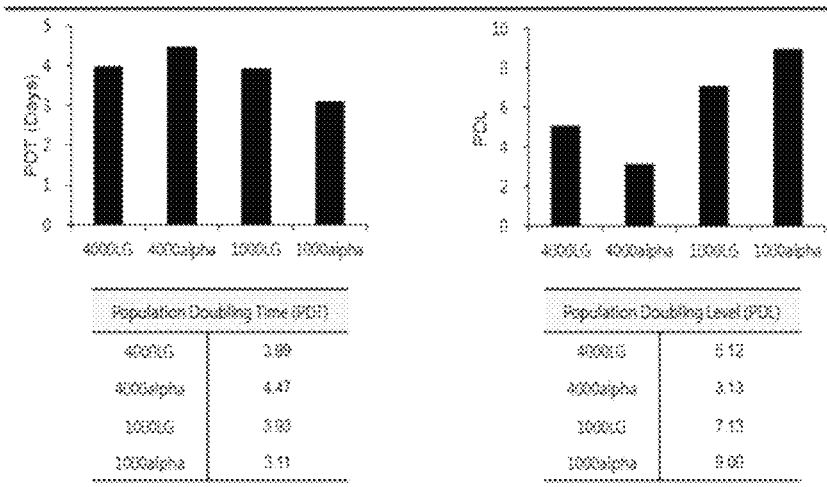
Figure 15:
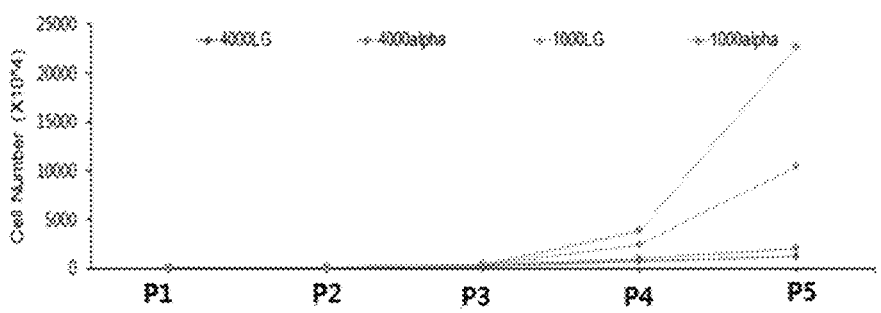
Figure 15:
Figure 16:
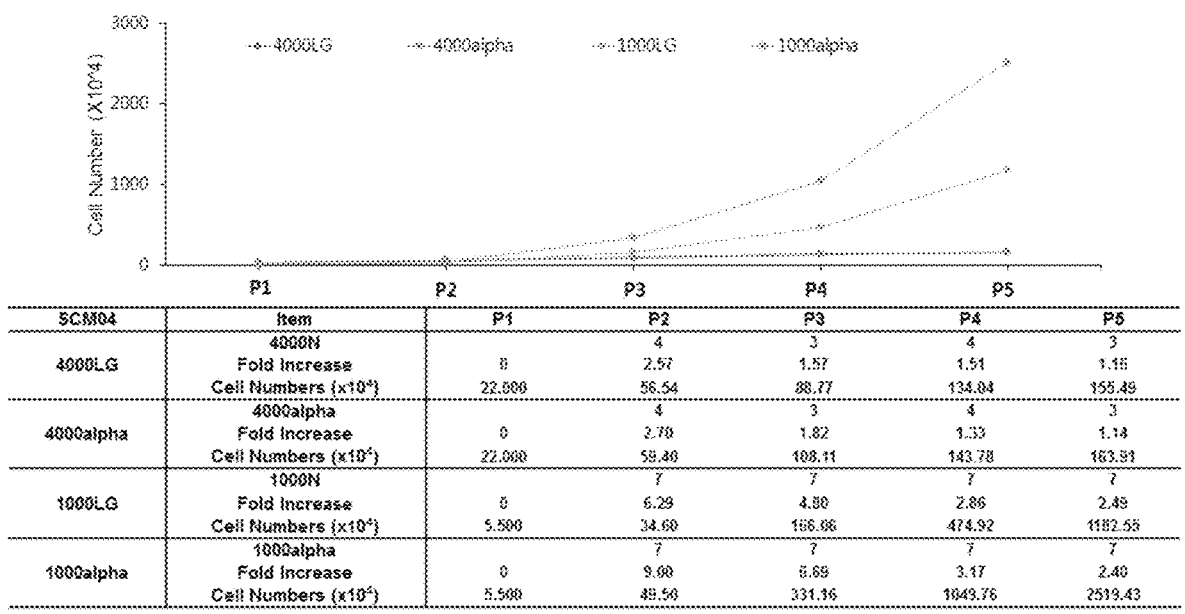
Figure 16:
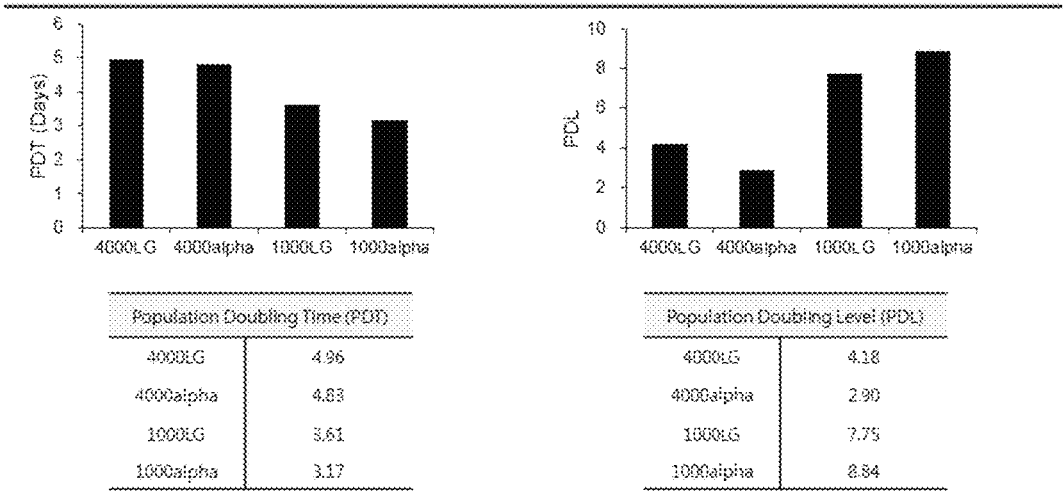
Figure 17:
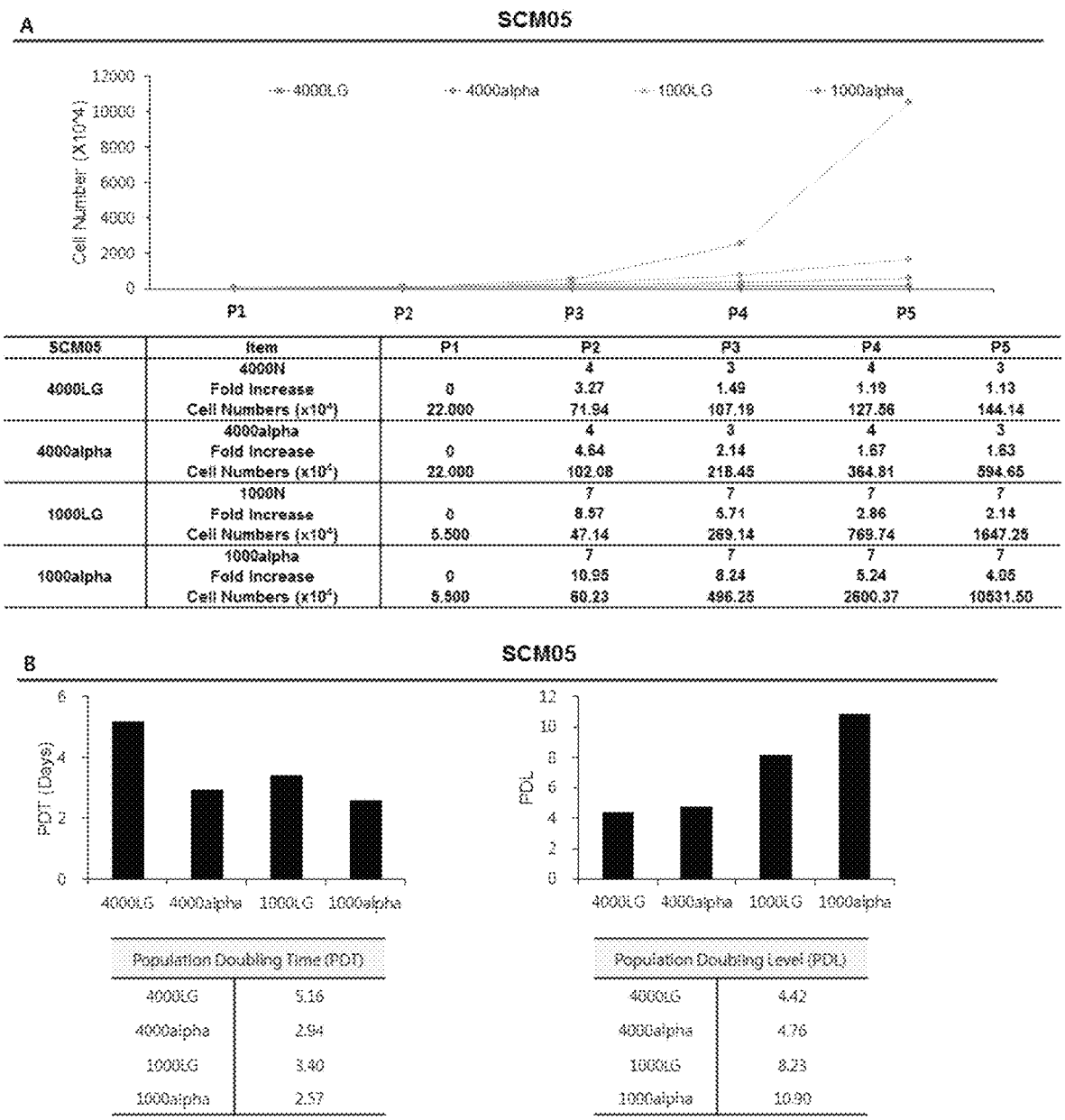
Figure 18:
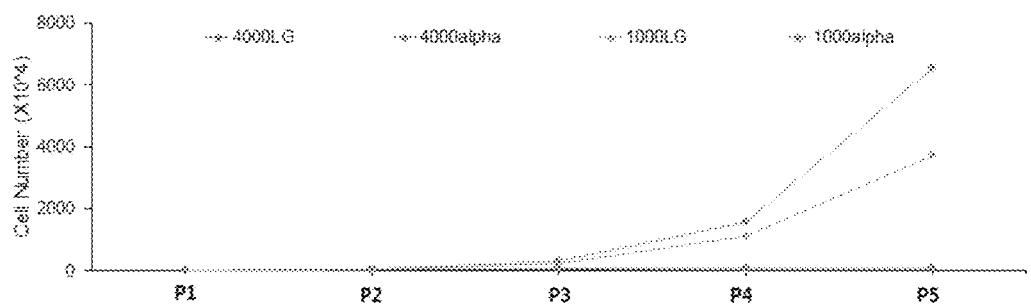
Figure 18:
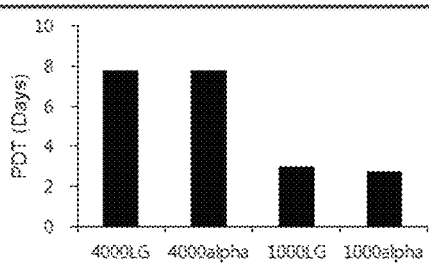
Figure 18:
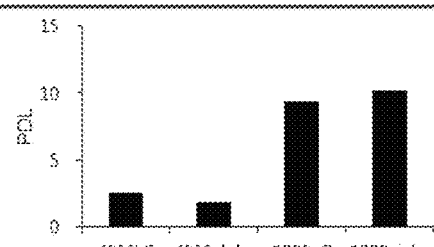
Figure 19:
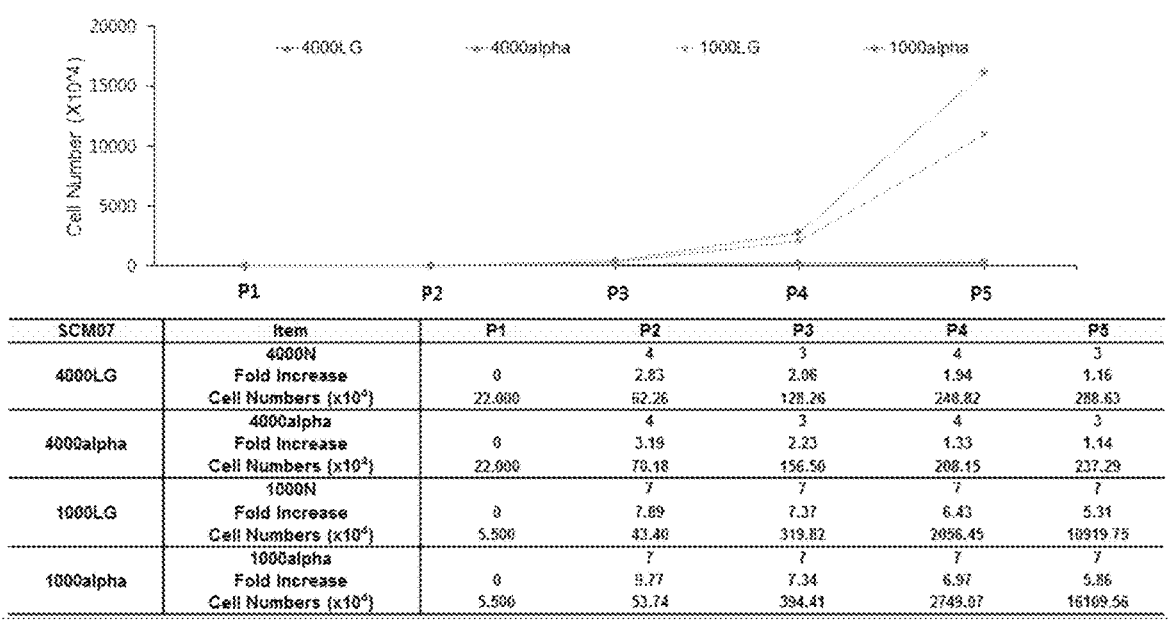
Figure 19:
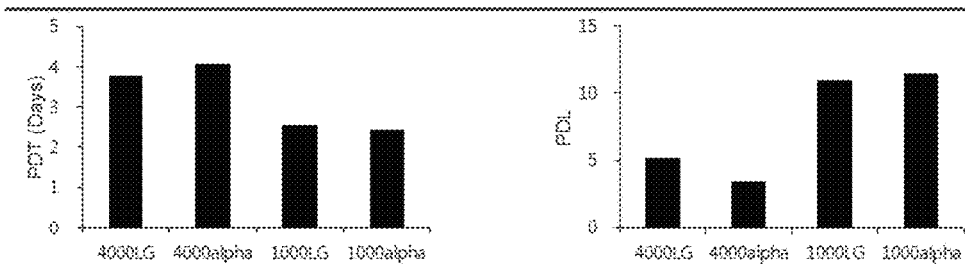
Figure 20:
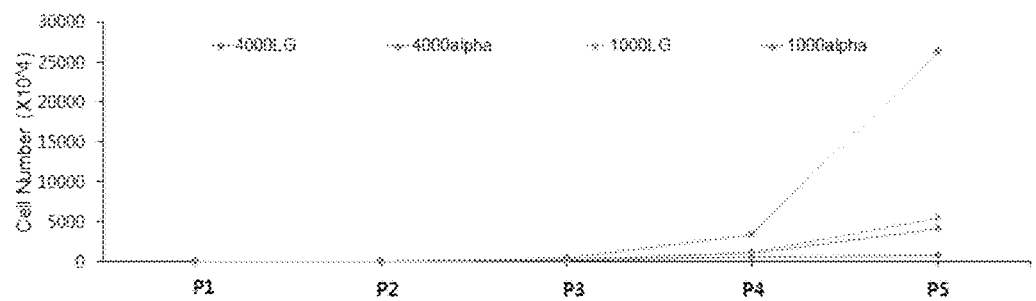
Figure 20:
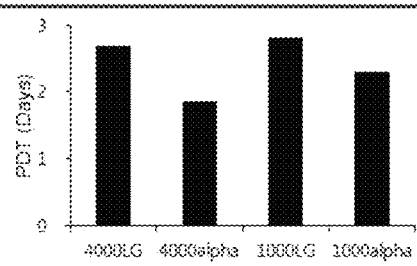
Figure 20:
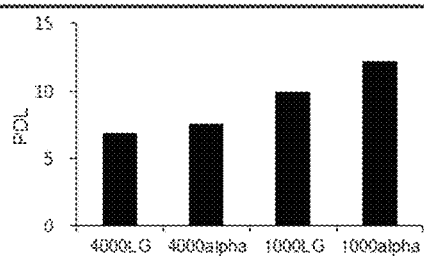

As shown in FIG. 12A, the conventional subfractionation culturing method and the improved subfractionation culturing method proceed in the same way until the process of obtaining the passage 1. The improved subfractionation culturing method proceeds in a differ manner from the conventional subfractionation culturing method after the step of culturing using the expanded passage 1 cell as the seed cell. The conventional subfractionation culturing method performs subculturing at a high density higher than or equal to 4000 cells/cm$^2$ for the purpose of obtaining many cells without recognition of the density control. In the improved subfractionation culturing method, the cell density in the subculturing is adjusted to the density lower than or equal to 1000 cells/cm$^2$ as a low density to culture the cells only to up to the passage 8 subsequent to the passage 2 to obtain the final product. The culturing process after the passage 2 is shown in detail in FIG. 12B.

TABLE 3

| Group | Culture density | Medium Condition | Passage | Subculturing Period (day) | Medium Change |
| --- | --- | --- | --- | --- | --- |
| 4000 LG | 4000 cells/cm$^2$ | LG-DMEM | P2-P5 | 3-4 | X |
| 4000 alpha | 4000 cells/cm$^2$ | alpha-MEM | | 3-4 | X |
| 1000 LG | 1000 cells/cm$^2$ | LG-DMEM | | 7 | O (every 3-4 days) |
| 1000 alpha | 1000 cells/cm$^2$ | alpha-MEM | | 7 | O (every 3-4 days) |

Cell lines of the above Table 3 were isolated by the subfractionation culturing method, and are named as SCM01 to SCM08, respectively.

2.1 Identification of proliferation effect according to cell line density and medium The cells were cultured using the SCM01 to SCM08 cell lines. To identify the cell proliferation effect according to subculture up to passage 5 lower than passage 10, the cell number, population doubling time (PDT) and population doubling level (PDL) were compared, respectively. The results are illustrated in FIGS. 13 to 20.

As illustrated in FIGS. 13 to 20, the cell proliferation effect of all experimental groups inoculated and cultured with a cell density of 1000 cells per cm$^2$ was superior to those of experimental groups inoculated and cultured with a cell density of 4000 cells per cm$^2$. Furthermore, even in the same 1000 cell density group, the 1000-alpha experimental group cultured in α-MEM containing ascorbic acid as an antioxidant showed more significant cell proliferation effect than other groups.

2.2 Comparison of Proliferation Effect According to Cell Line Density

For a more accurate comparison of the proliferation rate according to the number of cultured cells, LG-DMEM and α-MEM medium, respectively, were set as a culture medium, and the cell inoculation density was set as 1000 and 4000 cells/cm$^2$, respectively. Accordingly, the cell proliferation effect according to subculture was compared. The results are illustrated in FIGS. 21 to 24.

Figure 21:
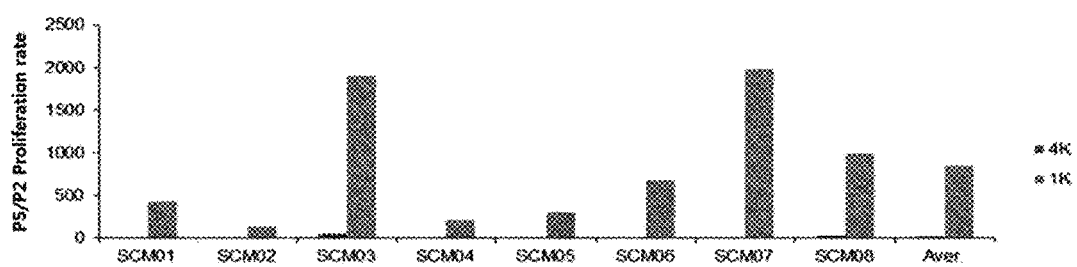
FIG. 21 illustrates the results of identifying proliferation rate of cells of each of experimental groups in which the monoclonal mesenchymal stem cells are inoculated at the density of 1000 or 4000 cells/cm$^2$, and the cells are cultured using the LG-DMEM culture medium without an antioxidant.

As illustrated in FIG. 21, when the SCM01 to SCM08 cell lines inoculated with 1000 cells/cm$^2$ were cultured in LG-DMEM, the proliferation rate of passage 2 (P2) to passage 5 (P5) was significantly higher than that of the group inoculated with 4000 cells/cm$^2$. The proliferation rate of the group inoculated with 1000 cells/cm$^2$ was at least 3.08 to at most 48.50 times compared with those of the group inoculated with 4000 cells/cm$^2$ in passage 5 (P5).

Figure 22:
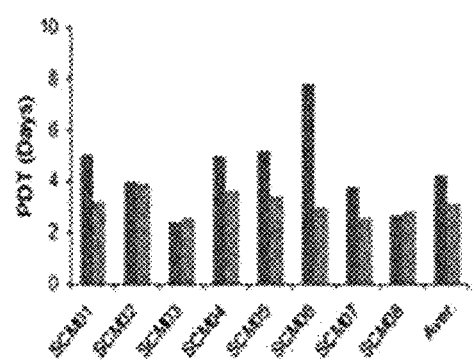
FIG. 22 illustrates the results of PDT and PDL of each of experimental groups in which the monoclonal mesenchymal stem cells are inoculated at the density of 1000 or 4000 cells/cm$^2$, and the cells are cultured using the LG-DMEM culture medium without an antioxidant.
Figure 22:
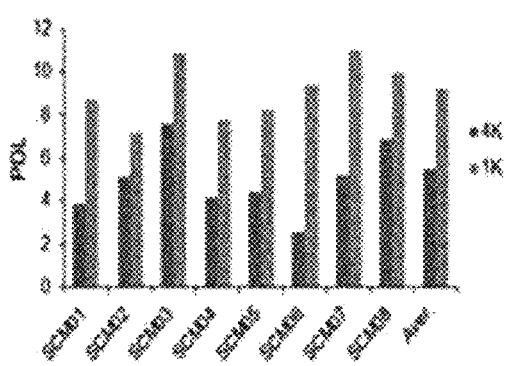

Further, as illustrated in FIG. 22, the PDT value of the group inoculated with 1000 cells/cm$^2$ was also lower or similar to those of 4000 cells/cm$^2$ inoculation in all cell lines, and the PDL value was higher than those of 4000 cells/cm$^2$ inoculation in all cell lines.

Figure 23:
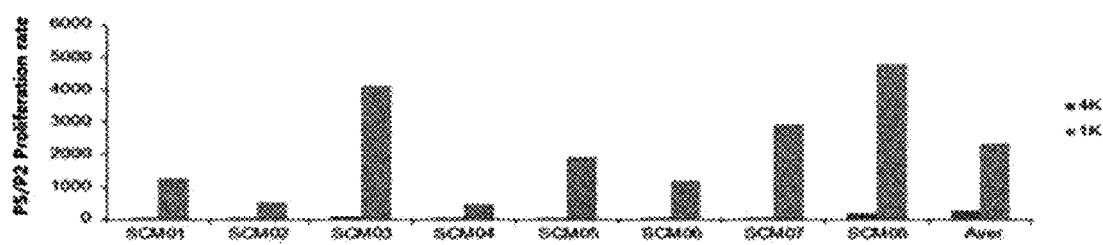
FIG. 23 illustrates the results of identifying proliferation rate of cells of each of experimental groups in which the monoclonal mesenchymal stem cells are inoculated at the density of 1000 or 4000 cells/cm$^2$, and the cells are cultured using the α-MEM culture medium with an antioxidant.
Figure 24:
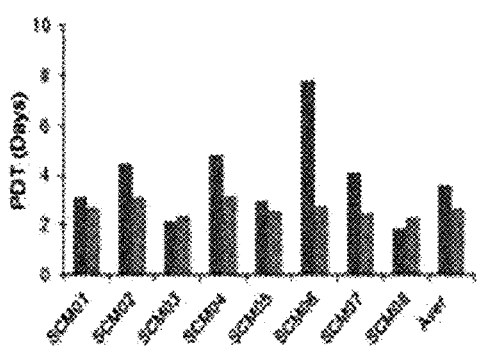
FIG. 24 illustrates the results of PDT and PDL of each of experimental groups in which the monoclonal mesenchymal stem cells are inoculated at the density of 1000 or 4000 cells/cm$^2$, and the cells are cultured using the α-MEM culture medium with an antioxidant.
Figure 24:
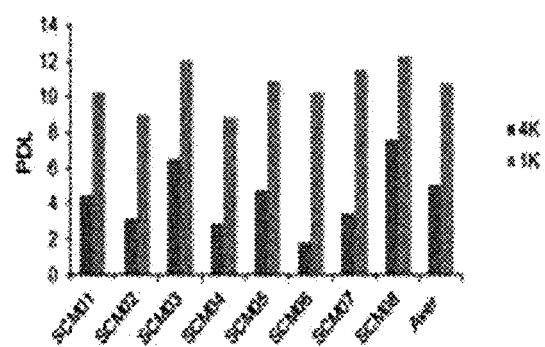

Further, as illustrated in FIG. 23, when all SCM01 to SCM08 cell lines cultured in α-MEM were inoculated and cultured with 1000 cells/cm$^2$, their tendency was similar to those of DMEM experimental groups. The proliferation rate of the group inoculated with 1000 cells/cm$^2$ was at least 6.32 to at most 85.63 times compared with those of the group inoculated with 4000 cells/cm$^2$ in passage 5 (P5). Further, as illustrated in FIG. 24, the PDT value was also lower or similar to those of 4000 cells/cm$^2$ inoculation in all cell lines, and the PDL value was higher than those of 4000 cells/cm$^2$ inoculation in all cell lines.

These results demonstrate that the inoculation with 1000 cells/cm$^2$ or less may induce rapid proliferation of monoclonal mesenchymal stem cells compared to high density cell line inoculation of 4000 cells per cm$^2$.

2.3 Comparison of Proliferation Effect According to Culture Medium

Example 2.2 confirmed that 1000 cells/cm$^2$ culture showed excellent proliferation effect compared with 4000 cells/cm$^2$ culture. Therefore, the experiment was conducted to compare the cell proliferation effect while the number of cells was fixed to 1000 cells/cm$^2$, and the medium varied as a variable. Thus, the proliferation effect was further verified according to the culture medium conditions. The results are illustrated in FIGS. 25 and 26.

Figure 25:
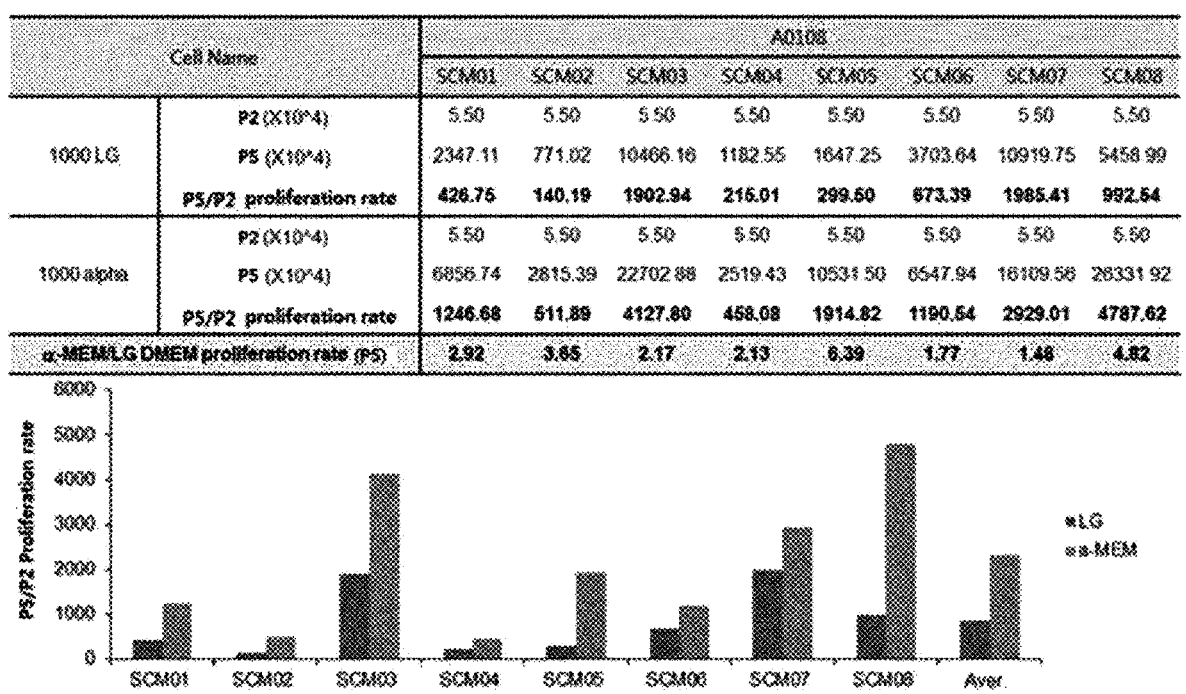
FIG. 25 illustrates the results of identifying the cell proliferation rate of each of experimental groups in which the cell density is fixed at the density of 1000 cells/cm$^2$, and the culture medium is LG-DMEM or α-MEM.
Figure 26:
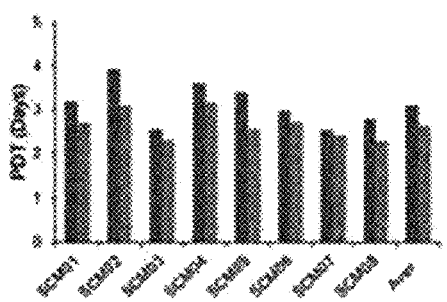
FIG. 26 illustrates the results of identifying PDT and PDL of each of experimental groups in which cell density is fixed at the density of 1000 cells/cm$^2$, and the culture medium is LG-DMEM or α-MEM.
Figure 26:
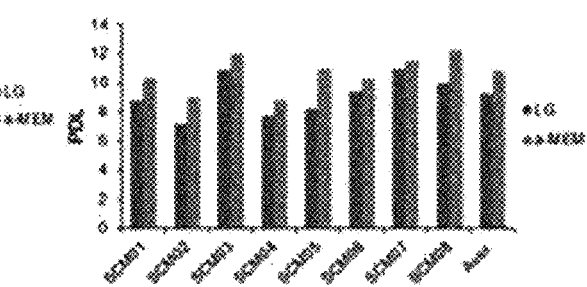

As illustrated in FIG. 25, the cell proliferation rates were compared between α-MEM and DMEM. The results showed that the proliferation rate of the group using α-MEM was at least 1.77 to 6.39 times compared with those of the group using LG-DMEM. Further, as illustrated in FIG. 26, the PDT was low in all α-MEM experimental groups and the PDL was increased in all α-MEM experimental groups.

These results indicate that the cell proliferation efficiency may be maximized by culturing cells using a medium containing an antioxidant in addition to manipulation of the cell inoculation density of 1000 cells or less per cm$^2$ and culture of the cells in passage 2 (P2) to passage 5 (P5) lower than the passage 10.

Example 3. Establishment of Improvement Process

Examples, as described above, confirmed that the control of cell density and the addition of an antioxidant might be important factors in the MSC culture. Based on the conventional subfractionation culturing method described in Korean Patent Application Nos. 10-2006-0075676 and 10-2014-0170045, the improvement process was carried out by varying the cell culture density and the medium conditions for effectively obtaining single colony mesenchymal stem cells at the passage lower than the passage 10. These are collectively shown in the following Table 4 (culture conditions using DMEM medium) and Table 5 (culture conditions using α-MEM medium).

TABLE 4

| Process | Items | Fresh Product | Frozen Product |
| --- | --- | --- | --- |
| Bone marrow to MCB *seed cell (excluding P1) | Culture medium | DMEM | DMEM |
| | Antibiotic (concentration) | Penicillin-streptomycin Penicillin (100 units/mL) Streptomycin (100 μg/mL) | Penicillin-streptomycin Penicillin (100 units/mL) Streptomycin (100 μg/mL) |
| | Cell culturing density | 50 to 1000 cells/cm$^2$ | 50 to 1000 cells/cm$^2$ |
| | Subculturing Period | 3 to 14 days | 3 to 14 days |
| | Passage | P1 to P8 | P1 to P8 |

TABLE 4-continued

| Process | Items | Fresh Product | Frozen Product |
|---|---|---|---|
| MCB to WCB | Culture medium | DMEM | DMEM |
| | Antibiotic (concentration) | Penicillin-streptomycin Penicillin (100 units/mL) Streptomycin (100 μg/mL) | Penicillin-streptomycin Penicillin (100 units/mL) Streptomycin (100 μg/mL) |
| | Cell culturing density | 50 to 1000 cells/cm$^2$ | 50 to 1000 cells/cm$^2$ |
| | Subculturing period | 3 to 14 days | 3 to 14 days |
| | Passage | P3 to P5 | P3 to P5 |
| Final product | Culture medium | DMEM | DMEM |
| | Antibiotic (concentration) | Penicillin-streptomycin Penicillin (100 units/mL) Streptomycin (100 μg/mL) | Penicillin-streptomycin Penicillin (100 units/mL) Streptomycin (100 μg/mL) |
| | Cell culturing density | 50 to 1000 cells/cm$^2$ | 50 to 1000 cells/cm$^2$ |
| | Subculturing period | 3 to 14 days | 3 to 14 days |
| | Passage | P6 to P8 | P6 to P8 |

TABLE 5

| Process | Items | Fresh Product | Frozen Product |
|---|---|---|---|
| Bone marrow to MCB *seed cell (excluding P1) | Culture medium | α-MEM | α-MEM |
| | Antibiotic (concentration) | Gentamicin (20 μg/mL) | Gentamicin (20 μg/mL) |
| | Cell culturing density | 50 to 1000 cells/cm$^2$ | 50 to 1000 cells/cm$^2$ |
| | Subculturing period | 3 to 14 days | 3 to 14 days |
| | Passage | P1 to P8 | P1 to P8 |
| MCB to WCB | Culture medium | α-MEM | α-MEM |
| | Antibiotic (concentration) | Gentamicin (20 μg/mL) | Gentamicin (20 μg/mL) |
| | Cell culturing density | 50 to 1000 cells/cm$^2$ | 50 to 1000 cells/cm$^2$ |
| | Subculturing period | 3 to 14 days | 3 to 14 days |
| | Passage | P3 to P5 | P3 to P5 |
| Final product | Culture medium | α-MEM | α-MEM |
| | Antibiotic (concentration) | Gentamicin (20 μg/mL) | Gentamicin (20 μg/mL) |
| | Cell culturing density | 50 to 1000 cells/cm$^2$ | 50 to 1000 cells/cm$^2$ |
| | Subculturing period | 3 to 14 days | 3 to 14 days |
| | Passage | P6 to P8 | P6 to P8 |

More specifically, the subfractionation culture process and proliferation culture of the bone marrow-derived mesenchymal stem cells in accordance with the present disclosure were performed as follows.

The hip of a bone marrow donor was anesthetized with local anesthetics. Then, the bone marrow was collected by piercing the needle into the hip bone. 14 ml Dulbecco's modified Eagle's medium (DMEM, GIBCO-BRL, Life-technologies, MD, USA) containing 20% FBS and 1% penicillin/streptomycin, and 1 ml human bone marrow were placed in a 100 mm culture vessel, and the mixture was cultured in a 5% $CO_2$ cell incubator at 37° C. for 2 hours. After the culture, the culture vessel was slightly tilted to one side, and only the supernatant of the culture vessel was transferred to a new vessel while the cells attached to the bottom were prevented from falling down.

The same procedure was repeated one more time, and the resulting culture solution was transferred to a culture vessel (Becton Dickinson) coated with collagen on the bottom thereof and cultured at 37° C. for 2 hours. The culture solution was transferred to a new vessel coated with collagen. After 24 hours, the culture solution was transferred to a new vessel. Again, after 24 hours, the culture solution was transferred to a new vessel. Finally, again, after 48 hours, the culture solution was transferred to a new vessel. Then, it was visually confirmed that remaining cells were grown and adhered to the bottom of the culture vessel. It may be assumed that cells which may come up to this step through the subfractionation culture process have much smaller than other cells.

After about 10 days to about 14 days, the cells formed a single colony. These monoclonal cell groups were treated with trypsin to be isolated. Then, the cells were transferred to a 6-well culture vessel. The cells were cultured in a 5% $CO_2$ cell incubator at 37° C. for 4 to 5 days. Then, when the cells were grown to about 80%, the cells were treated with 0.05% trypsin/1 mM EDTA (GIBCO-BRL), thereby obtaining the cells. Then, the cells were transferred to T175 culture vessel and subcultured at the lower cell density.

When the cells were cultured at a cell density which was reduced to 1000 cells/cm$^2$ in the early passage 2 (P2) to passage 5 (P5) lower than passage 10, preferably, lower than or equal to passage 8, but other procedures were regulated in the same manner, the proliferation ability and stem cell characteristics of MSCs were excellently maintained to induce efficient proliferation even in the same passage. In particular, when the cells were cultured at a cell density lowered as described above, it may exclude a process of preparing a working cell bank (WCB) in MSCs, which is required in the conventional process, thereby shortening the cell production period efficiently. In particular, when the passage number is lowered, cells with less aging may be obtained in a large amount. It is expected that such cells are used as a therapeutic agent to lead to excellent therapeutic effect.

Further, when α-MEM supplemented with an antioxidant is used as a culture medium, the antioxidant treatment may effectively reduce the ROS stress induced in high density cell culture and restore the cell proliferation ability of MSCs, thereby shortening the cell passage significantly and rapidly and stably obtaining single colony MSCs in a fresh state without aging, which maintains the characteristics of MSCs, compared to the conventional process.

In summary, the low density cell culture may not only obtain a large number of cells in the short term, thereby simplifying the production process, but also obtain cells with non-aging to maintain the intact characteristics of MSCs in the long-term culture. Therefore, this leads to high quality stem cell production.

Accordingly, stem cells obtained through the improvement method constructed through the Example in the experiment for the treatment of atopic dermatitis were used.

Example 4. Identification of Atopic Dermatitis Treatment Effect by Stem Cells Obtained Via Improved Subfractionation Culturing Method 4.1 Sample and Method Comparative experiments were performed to identify whether stem cells (hereinafter, referred to as GCM-MSC) obtained via the conventional density gradient centrifugation method (GCM) using Ficoll-Hypaque used to obtain stem cells and the monoclonal stem cell (hereinafter, referred to as SCM-cMSC) obtained via the improved subfractionation culturing method showed a difference in the atopic dermatitis treatment effect therebetween.

Samples used in the experiments are shown in Table 6 below. Egg white-derived albumin and aluminum hydroxide were used to induce atopic dermatitis. A Tegaderm film was used for dressing.

TABLE 6

|  | Lot. No. | Cat No. | Manufacturer |
| --- | --- | --- | --- |
| Albumin | SLBK1399V | A5503-5G | Sigma |
| Aluminum hydroxide (imjectAlum) | SD243749A | 77161 | Thermo scientific |
| Tegaderm film | 2019-08PE | 1624W | 3M |
| Cell Vehicle | Plasma Solution A: 67.5%, Human Serum Albumin: 22.5%, DMSO (Clinical grade): 10% | | |

Six-week-old SPF (specific pathogen-free) BALB/c mice (15 to 20 g) were used from SLC, Inc. (Suzuoka, Japan) to prepare an atopic dermatitis animal model. The experiment was started after a 1-week acclimatization period. To induce atopic dermatitis, 50 μg OVA (Ovalbumin) and 40 mg Alum Ajuvant were intraperitoneally and subcutaneously administered to 6-week-old BALB/c mice once a week for 3 weeks. After the inducer administration, a 1.2 cm×1.2 cm patch containing 60 μg OVA was attached to a depilated area twice for 2 weeks to induce atopy in BALB/c. After 20 days of sensitization, Cell vehicle, GCM-MSC, and SCM-cMSC were administered to the atopic dermatitis induced mice three times at two-day intervals through the caudal vein at the dosages shown in Table 7 below. 5 mice in which atopic dermatitis was not induced were set as a normal control.

TABLE 7

|  | First administration | Second administration | Third administration | Total administration amount |
| --- | --- | --- | --- | --- |
| Cell vehicle (N = 8) | 200 μl | 200 μl | 200 μl | 600 μl |
| GCM-MSC (N = 8) | 3.3 × 10$^5$/200 μl | 3.3 × 10$^5$/200 μl | 3.3 × 10$^5$/200 μl | 1 × 10$^6$/200 μl |
| SCM-cMSC (N = 8) | 3.3 × 10$^5$/200 μl | 3.3 × 10$^5$/200 μl | 3.3 × 10$^5$/200 μl | 1 × 10$^6$/200 μl |

To identify the effects on atopic dermatitis based on the administration, we identified changes in the expression of markers associated with the atopic dermatitis and related index in mouse skin, axillary lymph nodes (aLN), and blood.

4.2 Identifying Changes in Skin Lesions Based on SCM-cMSC Administration

SCM-cMSC and GCM-MSC were administered to the atopic dermatitis-induced animal model prepared in Example 4.1 in accordance with the above defined protocol, and, after 59 days, the change at the skin lesion was identified. The results are shown in FIG. 27.

Figure 27:
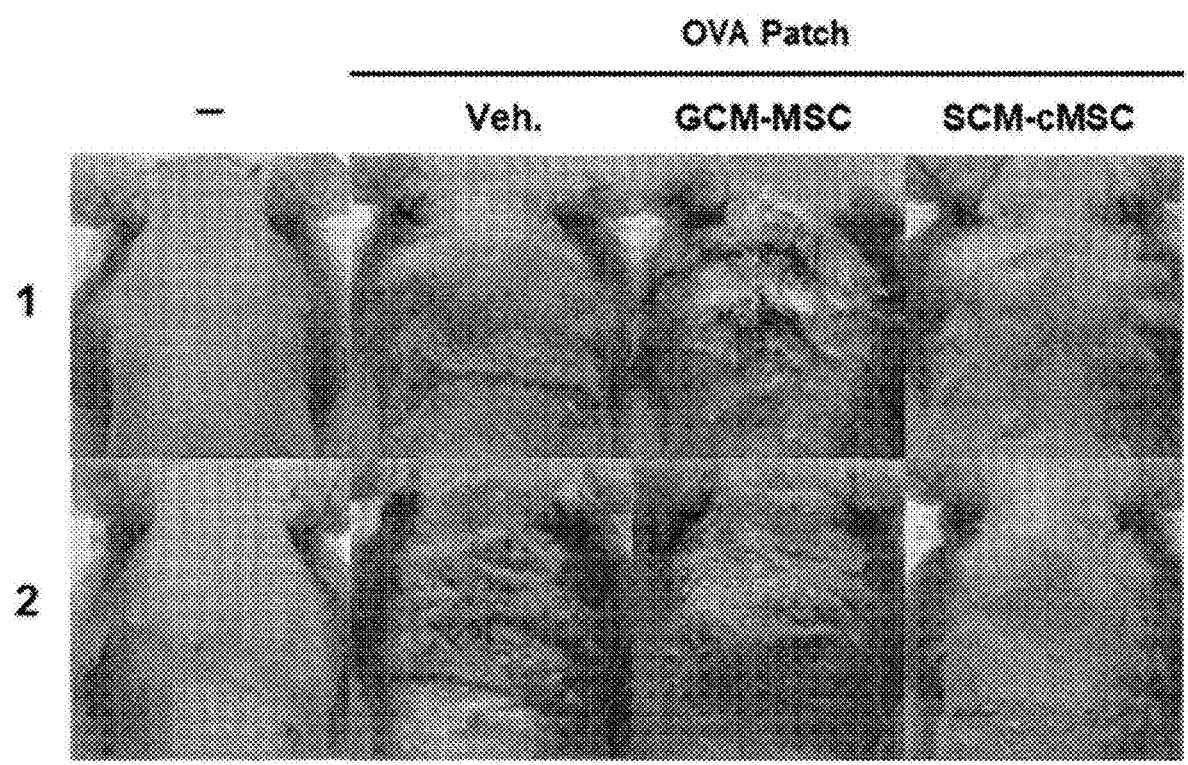
FIG. 27 shows the results of identifying changes of the skin lesion based on administration of a control (Cell Vehicle, veh), GCM-MSC, and SCM-cMSC to the atopic dermatitis animal model.

As shown in FIG. 27, the group subjected to administration of the SCM-cMSC as obtained through the improved subfractionation culturing method was found to have effectively reduced atopic dermatological lesions.

The back-skin tissue of the atopic dermatitis mouse model was treated with 10% formalin and fixed at 4° C. for 24 hours, and then was subjected to incision and dehydration and was fixed to paraffin. 4 μm thick cut sections were placed on slides, stained with H&E solution for 8 minutes, washed with alcohol. Then, we identified thickness changes and inflammatory infiltration of epidermis and dermis. Epidermis and dermis thicknesses were identified using a 200 magnification CaseViewer 1.4 software (3DHISTECH, BU, Hungary). Subsequently, in the same manner as the treatment with H&E, skin tissue treatment was performed and then toluidine blue staining was performed. Staining was performed for 2 to 3 minutes in a working solution, and the tissue was washed and dehydrated. The visual findings and the results of tissue staining are shown in Table 8 and FIG. 28 to FIG. 30.

TABLE 8

| | Epidermis (μm) | Dermis (μm) |
|---|---|---|
| Normal control | 54.48 | 223.1 |
| Atopic dermatitis model group, test substance non-treated group (Cell vehicle) (N = 8) | 108.9 | 786.7 |
| GCM-MSC (N = 8) | 100.5 | 672.7 |
| SCM-cMSC (N = 8) | 71.28 | 535.2 |

As shown in Table 8, in the SCM-cMSC treated group, the increase in epidermis and dermis thickness caused by atopic dermatitis was inhibited by up to 1.5-fold, compared with the cell vehicle. Further, in the SCM-cMSC treated group, the increase in epidermis and dermis thickness caused by atopic dermatitis was inhibited by 1.4-fold and 1.3-fold, compared with the GCM-MSC treated group. The SCM-cMSC treated group was identified to show significant improvement compared to the GCM-MSC treated group.

Figure 28:
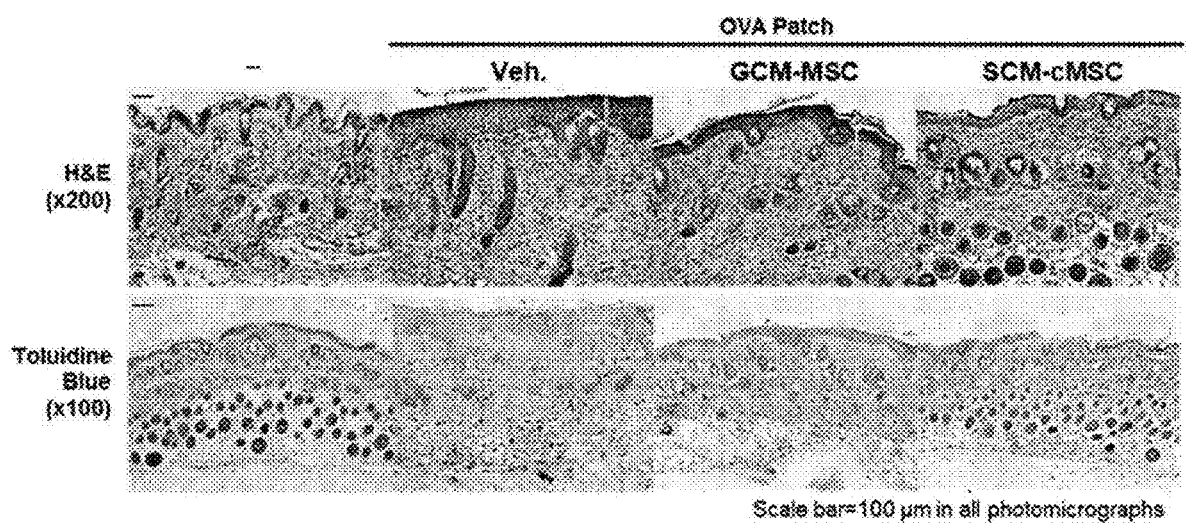
FIG. 28 shows the results of identifying change of the skin lesion based on administration of a control (Cell Vehicle, veh), GCM-MSC, and SCM-cMSC to the atopic dermatitis animal model via H&E and toluidine blue staining.
Figure 29:
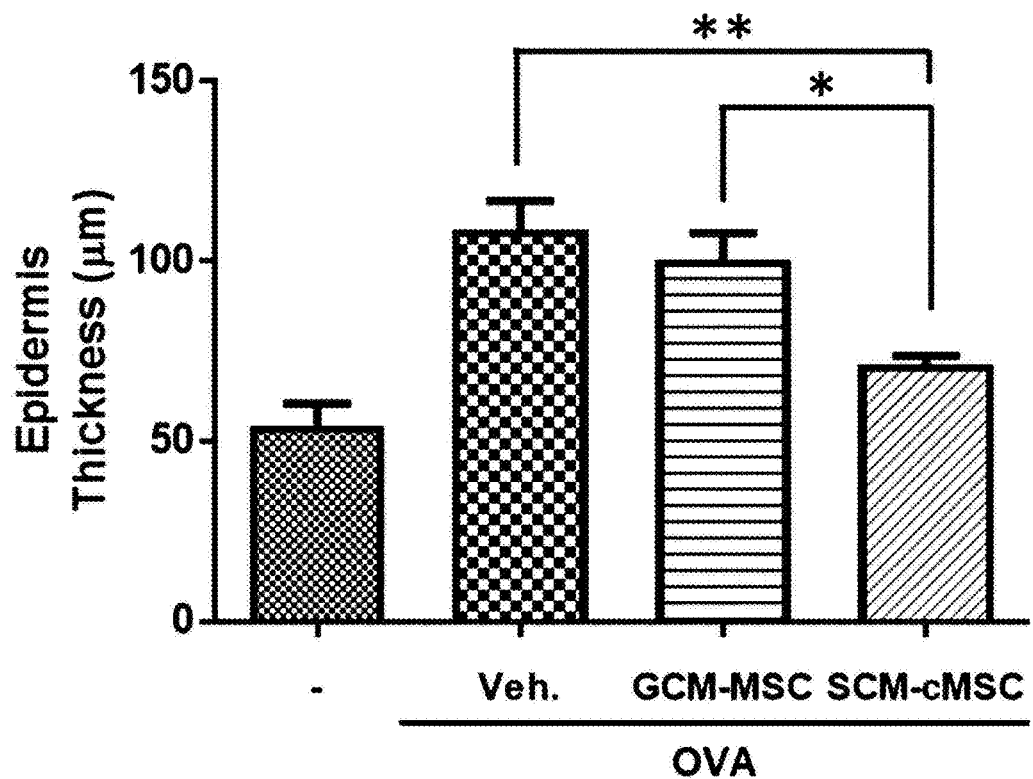
FIG. 29 shows the results of epidermis thickness changes based on administration of a control (Cell Vehicle, veh), GCM-MSC, and SCM-cMSC to the atopic dermatitis animal model (*P=0.0152, **P=0.0016).
Figure 30:
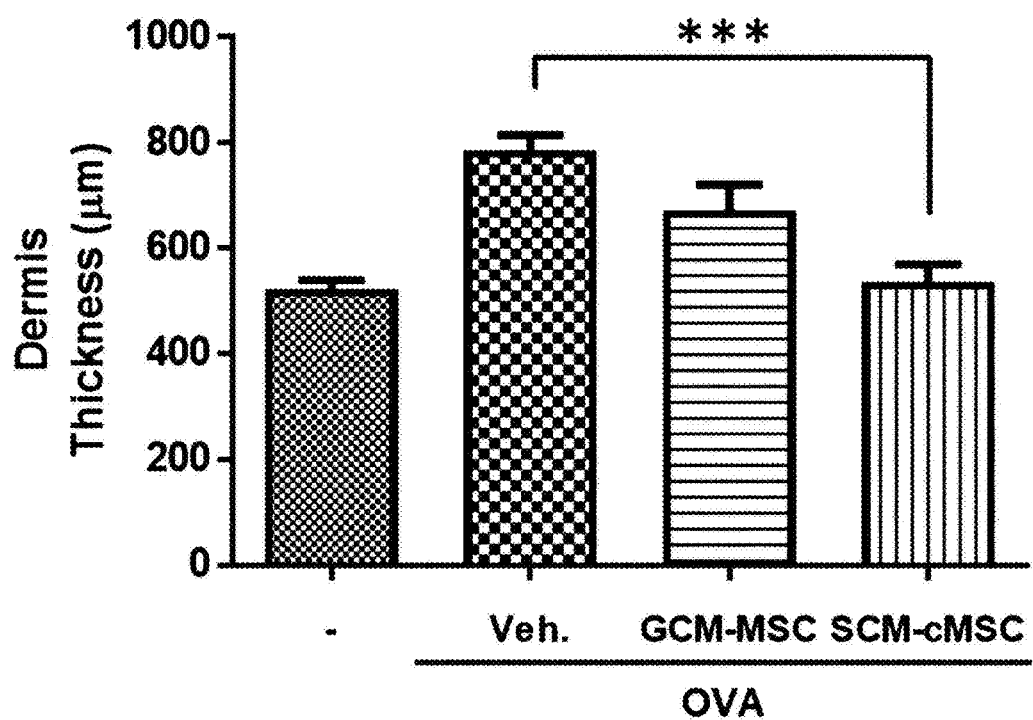
FIG. 30 shows the results of identifying dermis thickness changes based on administration of a control (Cell Vehicle, veh), GCM-MSC, and SCM-cMSC to the atopic dermatitis animal model (*** P=0.0003).

Further, as shown in FIG. 28 to FIG. 30, the histological analysis of the skin lesions showed a marked decrease in severe atopic symptoms in the SCM-cMSC treated group.

4.3 Identification of IgE, IgG1 Inhibitory Effect, and IgG2 Production Effect by SCM-cMSC Administration IgE and IgG1 production for four experimental groups were measured by ELISA and were compared with each other such that the effects of atopic dermatitis thereof were identified. Microwell plates were coated with 100 μl/well of capture antigen diluted in coating buffer for IgE analysis, the plates were sealed, and culturing was performed overnight at 4° C. The wells were subjected to absorption and were washed with wash buffer, the plate was upside down and the remaining buffer after the washing was removed. Plates were blocked with 200 μl/well Assay Diluent and the cells were incubated for 1 hour at room temperature. After washing, each experimental group was transferred to an appropriate plate. The cells in the sealed plate was cultured at room temperature for 2 hours, and the plate was washed again. We added 100 μl of a working detector (detection antibody and Say HRP reagent) thereto. Then, the cells were further cultured for 1 hour at room temperature. After addition of 100 μl of substrate solution to each well, the cells in the plate were cultured at room temperature for 30 minutes in a dark environment without the plate sealing and 50 μl of termination solution was added thereto. Absorbance at 450 nm was identified within 30 minutes from the termination reaction. We subtracted the absorbance value of 570 nm from the absorbance value of 450 nm. The results of identifying the effects of IgE and IgG1 production are shown in FIG. 31.

Figure 31:
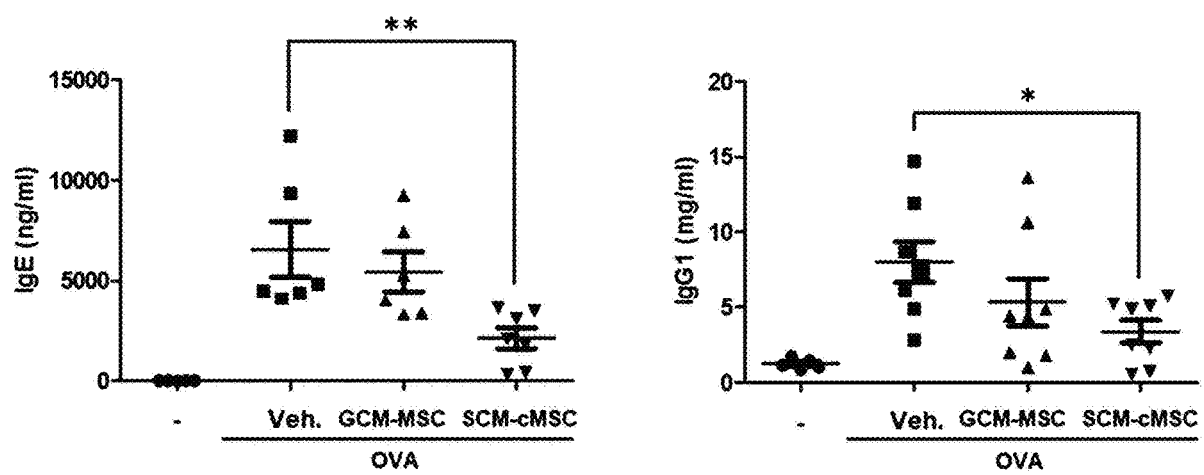
FIG. 31 shows the results of identifying changes in IgE and IgG1 production amounts based on administration of a control (Cell Vehicle, veh), GCM-MSC, and SCM-cMSC (IgE-P**=0.009, IgG1-P*=0.0432).

As shown in FIG. 31, the IgE and IgG1 production induced by the atopic dermatitis was markedly decreased due to administration of SCM-cMSC. This reduction effect is remarkably superior to that of GCM-MSC.

Additionally, ELISA methods were used to identify changes in IgG2a production. The results are shown in FIG. 32.

Figure 32:
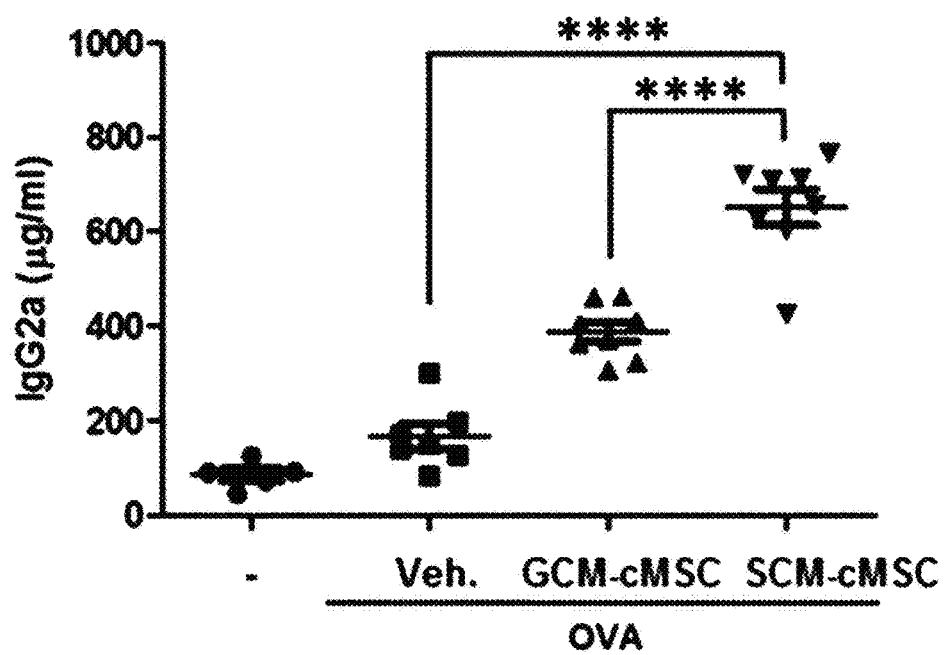
FIG. 32 shows the results of identifying IgG2a production amount changes based on administration of a control (Cell Vehicle, veh), GCM-MSC, and SCM-cMSC (P****<0.0001).

As shown in FIG. 32, the SCM-cMSC treated group was significantly superior to the GCM-MSC treated group in terms of the production of IgG2a. The production of IgG2a of the SCM-cMSC treated group has about three-fold increase over that of the atopic dermatitis model vehicle.

Figure 33:
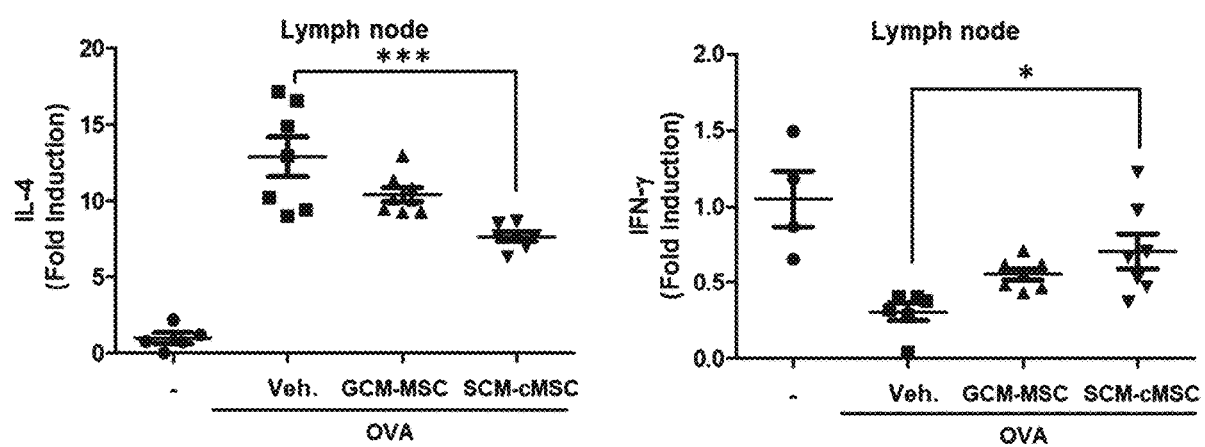
FIG. 33 shows the results of identifying changes in IL-4 and IFN-γ production amounts in axillary lymph nodes based on administration of a control (Cell Vehicle, veh), GCM-MSC, and SCM-cMSC (***P=0.0008, P*=0.0338).

4.4 Identification of IL-4 and IFN-γ Expression in Axillary Lymph Nodes Due to SCM-cMSC Administration Axillary lymph nodes were isolated from animal models having atopic dermatitis, and then, changes in IL-4 and IFN-γ expression in axillary lymph nodes based on SCM-cMSC and GCM-MSC administration thereto were identified using real-time PCR. Total RNA was obtained from axillary lymph nodes using TRIzol Reagent (Life technologies), and cDNA was prepared using primeScript™ RT reagent Kit with gDNA Eraser (TAKARA) according to instructions from the manufacturer. cDNA products were amplified using SYBR Green Quantitative PCR Master Mix (KAPA Biosystems). Primers were all purchased from Qiagen. The reaction was carried out in a StepOnePlus Real-Time PCR System (Applied Biosystems), and then PCR was performed under the following conditions for a total of 20 ml: denaturation for 5 minutes at 94.1° C.; amplification for 25 cycles for GAPDH, 30 s at 94.1° C., 30 s at 58.1° C. and 30 s at 72.1° C.; and elongation for 10 min at 72° C. Thereafter, 1 μl of each sample was placed on an agarose gel, stained with ethidium bromide, and visualized with ultra-violet light. Expression of each target gene was normalized using GAPDH, and the results are shown in FIG. 33. The information of the primers used in the experiment is as follows.

GAPDH Mm_Gapdh_3_SG QuantiTect Primer Assay Cat #QT01658692

IL-4 Mm_Il4_va.1_SG QuantiTect Primer Assay Cat #QT02418311

IFNγMm_Ifng_1_SG QuantiTect Primer Assay Cat #QT0103882115

As shown in FIG. 33, the increased IL-4 in the axillary lymph nodes of the atopic dermatitis model was decreased due to GCM-MSC and SCM-cMSC treatments, and the best decrease effect was identified from the SCM-cMSC treatment. Further, the level of the IFN-γ which was reduced in the atopic dermatitis model was markedly increased due to the SCM-cMSC treatment.

4.5 Measurement of Number of Mast Cells Due to SCM-cMSC Administration

In order to count mast cells, additional staining of skin tissue using Giemsa was performed. The number of infiltrated mast cells was counted using paint.NET at 100 magnification.

Figure 34:
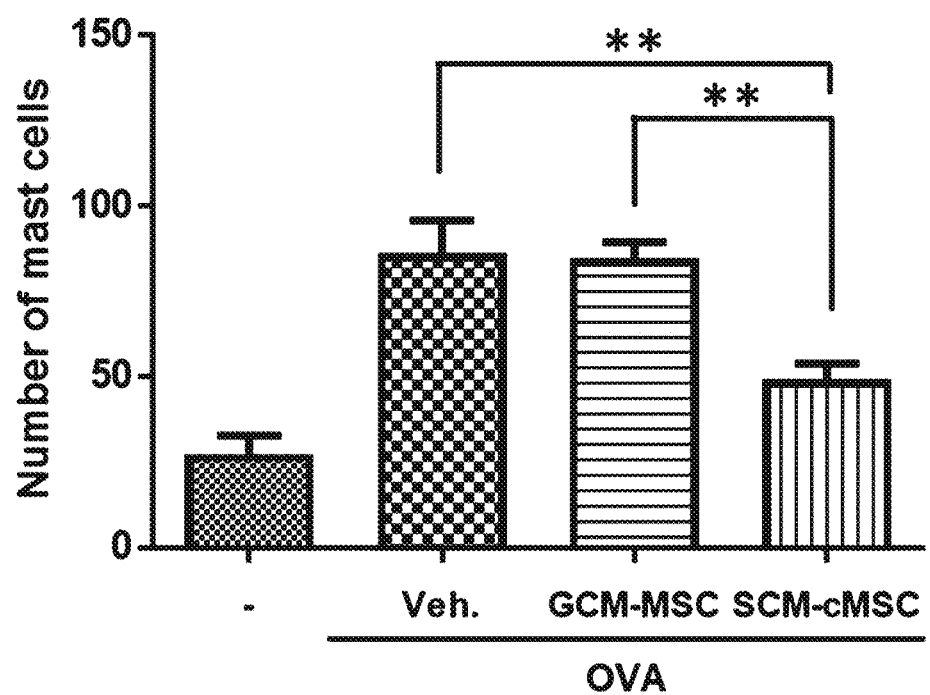
FIG. 34 shows the results of identifying changes in the number of mast cells based on administration of a control (Cell Vehicle, veh), GCM-MSC, and SCM-cMSC (P**=0.0026, 0.0036).

As shown in FIG. 34, in the atopic dermatitis model, mast cells were significantly increased (average 86) due to inflammation, compared to normal control. This increase was markedly reduced to an average of 49 due to the SCM-cMSC administration. This is a distinctive effect only in the SCM-cMSC administered group compared to the GCM-MSC administered group showing little mast cell reduction activity.

Example 5. Comparison of Atopic Dermatitis Treatment Effect According to Culturing Density 5.1 Preparation of cMSC1 and cMSC2

It was identified via Example 4 that cMSC obtained by the improved subfractionation culturing method via Examples 2 and 3 is obtained in the non-aged cell state that maintains the characteristics of mesenchymal stem cells (MSCs) even in long-term culturing, and that cMSC obtained by the improved subfractionation culturing method showed a significantly excellent atopic dermatitis treatment effect than GCM-MSC as a stem cell obtained by the conventional density gradient centrifugation method. Thus, the additional experiments were performed to identify whether there was a difference in the atopic dermatitis treatment effect between the cMSC obtained by the improved subfractionation culturing method including the low density culturing step and cMSC obtained by the conventional subfractionation culturing method including the high density culturing step.

According to the improved subfractionation culturing method of Example 3, monoclonal mesenchymal stem cells were obtained using α-MEM medium containing antioxidants while the cell culture density was set to 100 or 1000 cells/cm$^2$ in the subculturing. Gentamicin was used as antibiotic. α-MEM culturing solution was used (see Table 5). Hereinafter, stem cells obtained via the improved subfractionation culturing method at the low density of 100 or 1000 cells/cm$^2$ or less under the antioxidant condition was referred to as "cMSC1".

Further, to compare the effects between the stem cells obtained by the improved subfractionation culturing method, stem cells obtained by the conventional subfractionation culturing method at a high cell density of 4000 cells/cm$^2$ or greater under an antioxidant-free condition in subculturing was referred to as "cMSC2".

5.2 Experimental Material and Method

The animals used for the atopic dermatitis test were 6-week-old female SPF (specific pathogen-free) BALB/c mice (15 to 20 g) from SLC, Inc (Shizuoka, Japan). The experiment was performed after acclimatization period in the animal room for 1 week. In Inha University Medical Science Research Institute, 5 mice were raised in each of mouse cages at 150 to 300 Lux lighting at temperature of 22 to 25° C., a humidity 40 to 60%, day and night 12 hours alternately. Experiments were conducted to maintain a breeding environment so that sterile distilled water and solid feed could be freely consumed by the mice. Ovalbumin (OVA) 50 µg/50 µl (PBS) and Alum Adjuvant 4 mg/100 µl were mixed with each other and then the mixture was administered to 7-week-old female BALB/c mice in intraperitoneal and subcutaneous manners three times once a week for three weeks to induce sensitization of atopic dermatitis. All three administrations to the same site may induce inflammation irrelevant to the disease of interest. Thus, three administrations to different sites were performed. After 3 weeks from the OVA administration, 1.2× 1.2 cm sterile gauze moistened with OVA 60 µg/60 µl (PBS) was applied to the depilated back skin region three times per week for 2 weeks to induce the atopic dermatitis in a topical region. After the atopic dermatitis induction through OVA patch, the monoclonal stem cells were obtained through PBS and subfractionation culturing method at passage after passage 2 while varying the cell density to 100 cells/cm$^2$, 1000 cells/cm$^2$ and 4000 cells/cm$^2$. A total of three injections of the monoclonal stem cells to the mice via the caudal vein was performed at two-day intervals. The injection volume was 3.3×10$^5$/200 µl per time. Thu, intravenous administration of a total of 1.0×10$^6$/600 µl of the monoclonal stem cells to the mouse model was carried out. Two days after the administration, the affected area was re-depilated and then a 1.2×1.2 cm sterile gauze moistened with OVA 60 µg/60 µl (PBS) was applied to the re-depilated back skin region three to four times per week for 2 weeks to re-induce the atopic dermatitis in the topical region. 13 to 14 days after the induction of the atopic dermatitis, the experimental animals are calibrated with restrainers and the monoclonal stem cells were administered to the mouse model via caudal vein using a 1 ml syringe equipped with a 26½ gauge needle from BD company. Not the test substance but PBS was administered intravenously to animals of the Veh. group. The test substance was suspended in the PBS. The suspension as administered intravenously to animals of the experiment groups except for the Naïve and Veh. groups. Each of PBS and test substance was administered at the same amount of 200 µl/head.

Blood samples to identify effects on atopic dermatitis of the test substance were obtained in the following manner. All experimental animals were anesthetized with isoflurane on day 13 after administration of cell stabilizer or the test substance thereto. Then, the abdominal incision thereof was executed to expose the posterior vena cava, and about 700 µL blood was collected using a 1 ml syringe. The collected blood was input in Serum separate tube and serum was isolated after centrifugation at 3000 rpm/15 min at 4° C. The isolated serum was input in 1.5 ml e-tube which in turn was stored in −70° C. deep freezer.

In order to analyze the effect on atopic dermatitis by the test substance, serum samples of all animals were measured by using an ELISA kit to measure total IgE, IgG1 and IgG2a concentrations. The measurement method was performed according to the kit's protocol. Specifically, the blood IgE level was measured by inputting the blood collected through the posterior vena cava into the EDTA tube and executing centrifugation thereof for 3000 rpm/15 minutes to isolate only the supernatant which was stored at −70° C. until the experiment. Capture antibody that can recognize IgE together with coating buffer were stored on ELISA plate overnight at 4° C. After the blocking process for 1 hour the next day, the serum was diluted 100-fold and then an amount of 50 µL of the diluted serum reacted at room temperature for 2 hours. After the addition of a secondary antibody that recognizes IgE thereto, the TMB solution, as a substrate buffer was added thereto and the serum reacted for about 15 minutes. Then, 50 µl of stop solution was added thereto. The measurement was performed on a 450 nm filter using an ELISA reader.

At the end of the experiment, the extracted skin tissue was fixed in 4% formalin solution and thus tissue cut sections were made and stained with Hematoxylin & Eosin (H&E) and were stained with toluidine blue which stains infiltrated mast cells in dermis. The stained tissues were measured for the thickness of dermis and epidermis under 200 magnification of optical microscope. At 100-fold magnification, inflammatory cell infiltration and mast cell increase or decrease were measured. The skin thickness and mast cell measurements were performed using the PAINT.NET program.

Skin and axillary lymph nodes were sampled from all experimental animals. Then, expression levels of IL-4, IL-5, IL-10, IL-17, IL-31, TNF-α, TGF-γ, IFN-γ, TSLP and the like therein were measured using qPCR master mix. The measurement method was carried out according to the qPCR protocol. Specifically, mRNA was isolated from the skin tissue of the experimental animal for real-time PCR. RNA was obtained by injecting 1 ml trizol solution into skin tissue, grinding the same using a pestle, and then isolating the RNA. The genomic DNA elimination reaction was performed on the isolated RNA to convert 1 μg of isolated RNA into cDNA. Then, the reverse-transcription enzyme was added to cDNA which in turn was reacted for 20 minutes. Real-time PCR was performed using a SYBR FAST qPCR master mix that specifically binds to double DNA. Samples were prepared to have a volume of 20 μl having 5 μl of cDNA, 10 μl of qPCR master mix (2×), 1 μl of specific target primer, and 4 μl of DW. PCR proceeds in total 45 cycles. The ratio for correcting the target gene using GAPDH was quantified.

All measurements of the experimental results were calculated as mean±standard error. Statistical analysis was performed via 1Way ANOVA, Tukey's multiple comparison test using Prism 7.05 (GraphPad Software Inc., San Diego, Calif., USA). p value was determined to be significant in case of *$P<0.05$, $P<0.01$, *$P<0.001$.

5.3 Identifying of Body Weight and Cell Viability in Atopic dermatitis Animal Models Body weights for each group were measured at the time of sacrifice (D-59) in atopic dermatitis-induced animal models. The total cell number and cell viability by administration of cMSC1 and cMSC2 were identified using Automated Cell Counters and Cell Analyzers (NC-250™) method. The results are shown in FIG. 35 and FIG. 36.

Figure 35:
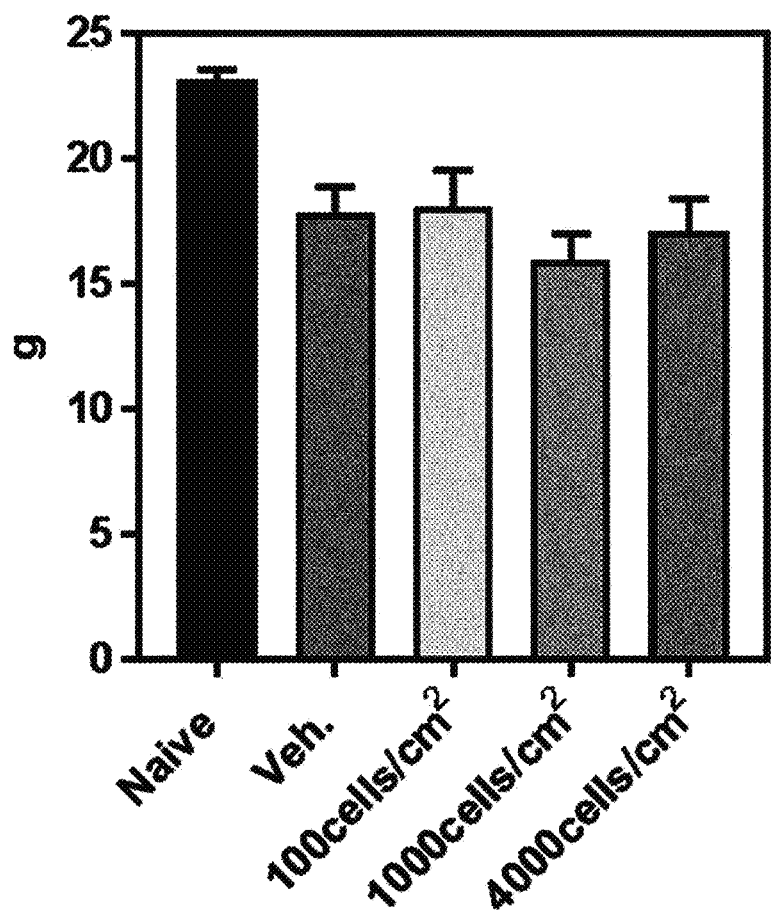
FIG. 35 shows the results of body weight change based on administration of a control (Cell Vehicle, veh), cMSC1 (100 or 1000 cells/cm$^2$), and cMSC2 (4000 cells/cm$^2$) to the atopic dermatitis animal model.
Figure 36:
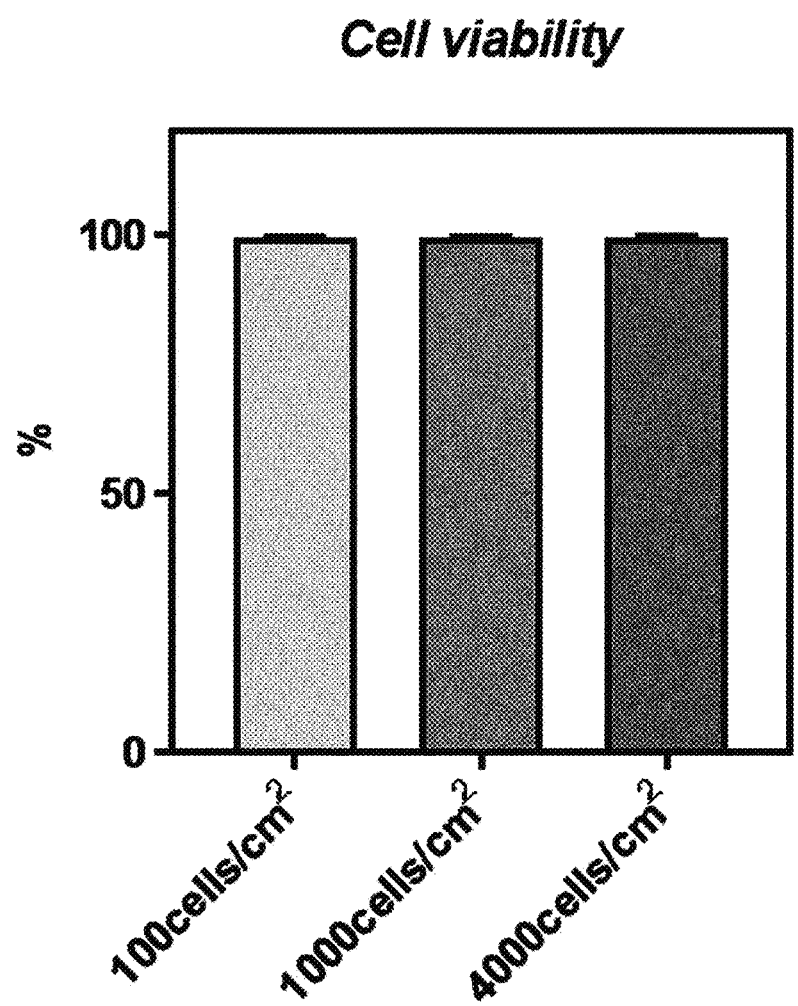
FIG. 36 shows the results of cell viability changes based on administration of cMSC1 (100 or 1000 cells/cm$^2$) and cMSC2 (4000 cells/cm$^2$) to the atopic dermatitis animal model.

As shown in FIG. 35, there was no difference between the weights of the animal models in which atopic dermatitis was induced and weights of the individual groups administered with cMSC1 and 2. As shown in FIG. 36, the average cell viability of the group injected with cMSC1 (100 cm$^2$ and 1000 cm$^2$) and cMSC2 (4000 cm$^2$) through caudal vein three times at two-day intervals was found to be greater than 90%.

5.4 Identification of Inhibitory Effects of IgE Expression

In Example 4.3, we found that administration of SCM-cMSC was superior to compared to GCM-MSC administration in terms of IgE inhibitory effect in atopic dermatitis animal model. Therefore, ELISA analysis was performed to identify whether IgE inhibitory effect was different in serum based on density difference of stem cells obtained by the subfractionation culturing method. More specifically, the atopic dermatitis animal model prepared in Example 5.2 was sacrificed at the time of D-59. Serum was obtained from blood collected via caudal vena cava at the time of sacrifice and IgE ELISA analysis was performed on the serum. The results are shown in FIG. 37.

Figure 37:
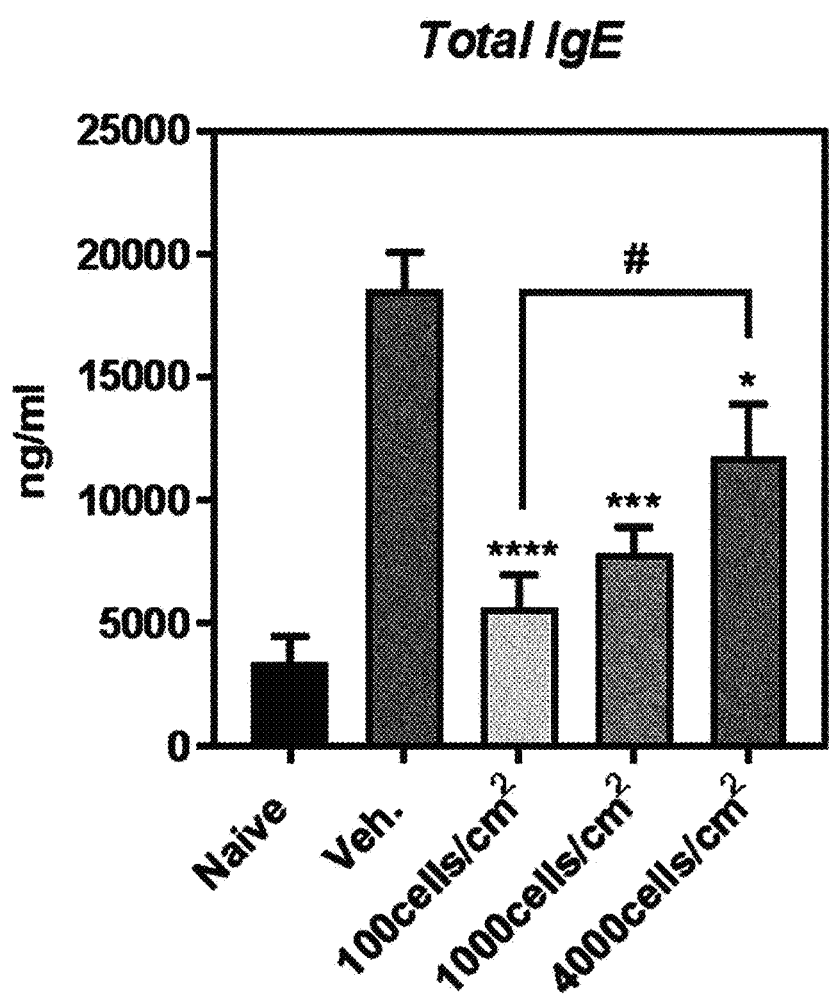
FIG. 37 shows ELISA analysis results of changes in total IgE production amount based on administration of a normal control (naïve), a control (Cell Vehicle, veh), cMSC1 (100 or 1000 cells/cm$^2$), and cMSC2 (4000 cells/cm$^2$) to the atopic dermatitis animal model (1way ANOVA—Tukey's multiple comparisons test **P<0.0001 *P=0.0001 *P=0.0238 compared to Veh. Unpaired t test—#P=0.0336 compared to 100 cells/cm$^2$ group).

As shown in FIG. 37, both cMSC1 and cMSC2 administered groups showed IgE inhibitory effect compared to the Vehicle treated group. The cMSC1 (100 or 1000 cells/cm$^2$) experimental group obtained by the improved subfractionation culturing method including the low density culturing exhibited excellent IgE inhibitory effect compared to the cMSC2 (4000 cells/cm$^2$) experimental group obtained by the subfractionation culturing method including the high density culturing. This result shows that the monoclonal stem cells obtained by culturing at low densities may significantly lower IgE levels, and thus have an excellent effect on atopic dermatitis.

5.4 Identifying of Visual Findings of Skin Lesions

PBC alone (Vehicle), cMSC1 (100 or 1000 cells/cm$^2$), and cMSC2 were applied to a total of seven atopic dermatitis mice prepared in Example 5.2. The recovery of atopic dermatitis at the skin lesion site was visually identified. The lesions were visually identified by comparing the degree of wound, erythema and keratin at the atopic dermatitis-induced back site. Changes in skin epidermis thickness were identified via H&E staining. The results are shown in FIG. 38 and FIG. 39.

Figure 38:
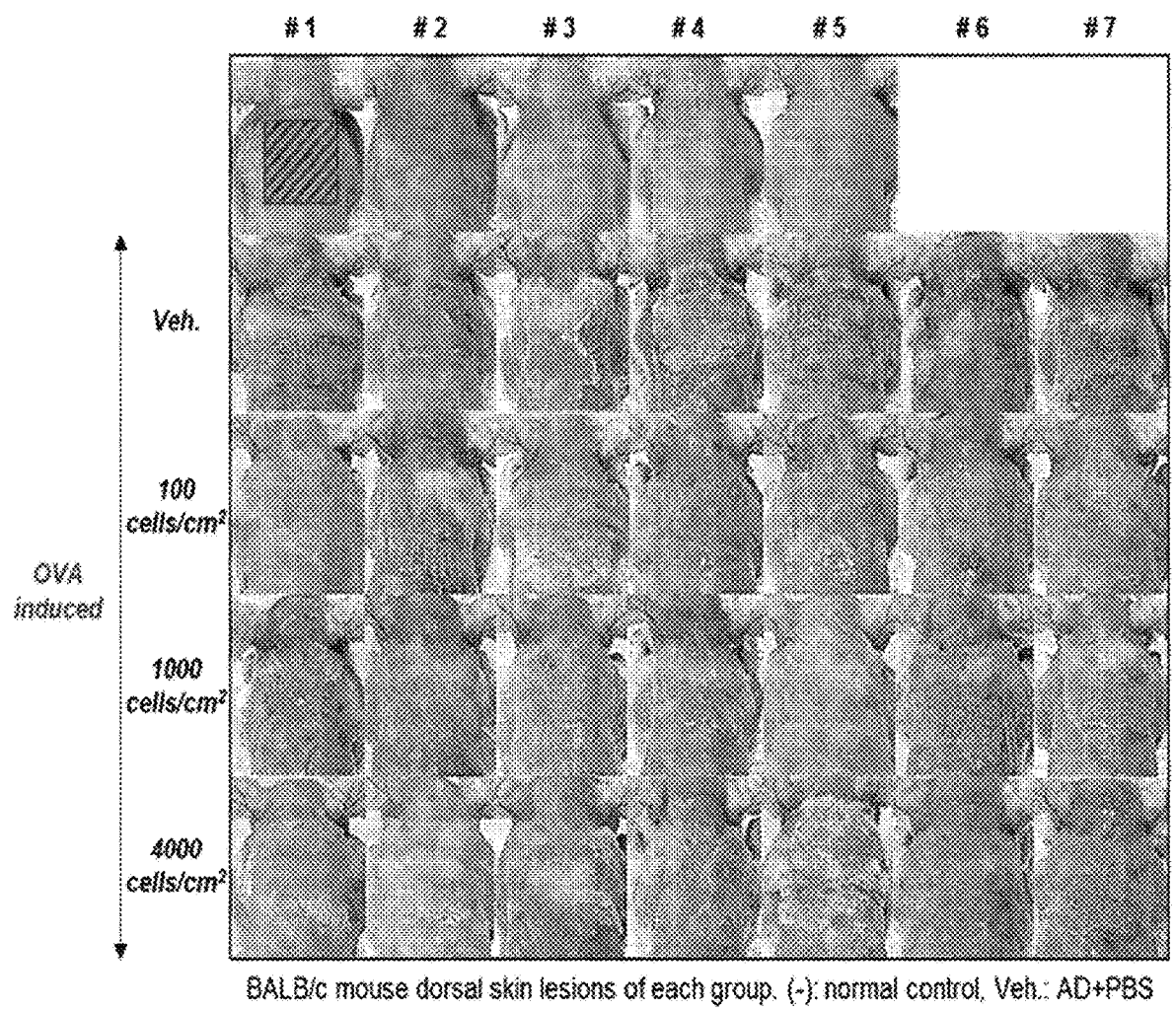
FIG. 38 identifies changes in skin lesions based on application of normal control (−), control (PBS, veh), cMSC1 (100 or 1000 cells/cm$^2$), and cMSC2 (4000 cells/cm$^2$) to the atopic dermatitis animal model.

As shown in FIG. 38, visually, the improvement of skin lesions was more visually identified in the cMSC1 (100 or 1000 cells/cm$^2$) group than in the cMSC2. Thus, the better lesion improvement effect was identified in the group applied with the stem cells at the lower density 100 cells/cm$^2$.

Figure 39:
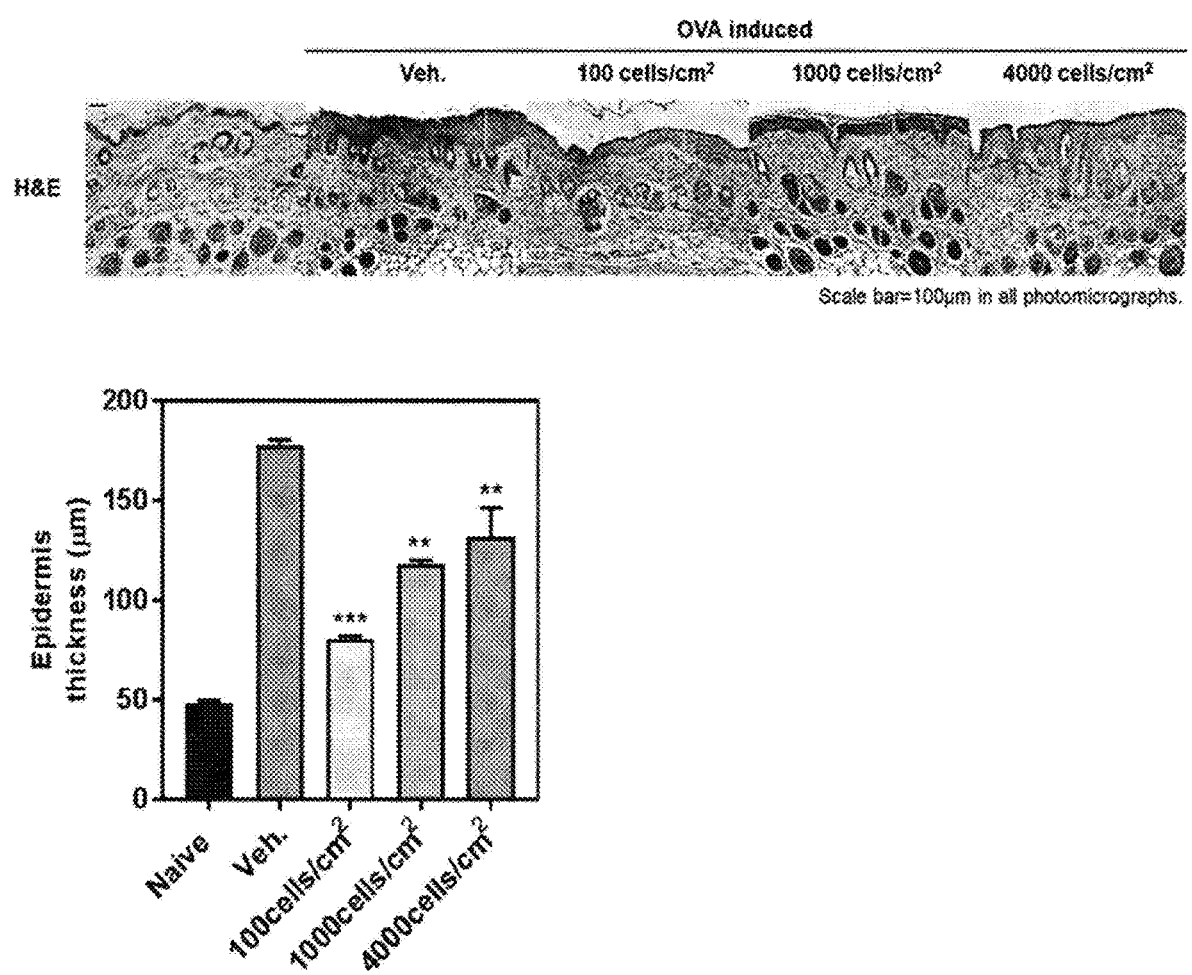
FIG. 39 identifies the effects of reduction of the epidermis thickening based on the application of normal control (−), control (PBS, veh), cMSC1 (100 or 1000 cells/cm$^2$), and cMSC2 (4000 cells/cm$^2$) to the atopic dermatitis animal model.

As shown in FIG. 39, it was observed that the cMSC1 (100 or 1000 cells/cm$^2$) group showed a clearer epidermis thickening reducing effect compared to the cMSC2.

In summary, the above results suggest that the use of cMSC1 obtained through the improved process can provide better anti-inflammatory effects and amelioration effect of the atopic dermatitis compared to the monoclonal stem cells obtained via the conventional density gradient subfractionation culturing method. Further, it was found that the stem cells (cMSC1) obtained by the improved subfractionation culturing method including the low density culturing steps may show better atopic dermatitis amelioration effect in comparison with the stem cell (cMSC2) obtained by subfractionation culturing method including the high density culturing step.

From the foregoing, it will be appreciated that various embodiments of the present disclosure have been described herein for purposes of illustration and that various modifications may be made without departing from the scope and spirit of the present disclosure. Accordingly, the various embodiments disclosed herein are not intended to be limiting, with the true scope and spirit being indicated by the following claims.

What is claimed is:

1. A method for treating atopic dermatitis in a subject comprising:
   1) culturing bone marrow isolated from an individual in a first vessel;
   2) transferring only a first supernatant in the first vessel to a second vessel;
   3) culturing cells present in the first supernatant in the second vessel and obtaining a second supernatant in the second vessel;
   4) sequentially repeating the steps 2) and 3) at least one time while the first supernatant in the step 2) is replaced with the second supernatant in the step 3), thereby obtaining a colony of monoclonal mesenchymal stem cells; and
   5) seeding the monoclonal mesenchymal stem cells from the step 4) into a culture medium at a cell density of 1000 cells/cm$^2$ in culture for passage 1; and
   6) subculturing the monoclonal mesenchymal stem cells for passages 2 to 8 and thereby obtaining a composition comprising the monoclonal mesenchymal stem cells,
   wherein the monoclonal mesenchymal stem cells reseeded at a cell density of 1000 cells/cm$^2$ for passages 2 to 8, wherein the culture medium in the steps 5) and 6) includes an antioxidant, and
   wherein the monoclonal mesenchymal stem cells are obtained without preparing a working cell bank; and
   7) administering the composition to the subject.

2. The method of claim 1, wherein the monoclonal mesenchymal stem cell reduces thickening of dermis or epidermis having atopic dermatitis.

3. The method of claim 1, wherein the monoclonal mesenchymal stem cells inhibits production of at least one species selected from a group consisting of IgE, IgG1 and IL-4 or promotes production of INF-γ in the subject.

4. The method of claim 1, wherein the monoclonal mesenchymal stem cells inhibit infiltration of mast cells in the subject.

5. The method of claim 1, wherein the composition is a pharmaceutical formulation, a quasi-drug formulation, or a cosmetic formulation.

6. A method for preparing a composition for treatment, or amelioration of atopic dermatitis, the method comprising:
   1) culturing bone marrow isolated from an individual in a first vessel;
   2) transferring only a first supernatant in the first vessel to a second vessel;
   3) culturing cells present in the first supernatant in the second vessel and obtaining a second supernatant in the second vessel;
   4) sequentially repeating the steps 2) and 3) at least one time while the first supernatant in the step 2) is replaced with the second supernatant in the step 3), thereby obtaining a colony of monoclonal mesenchymal stem cells; and
   5) seeding the monoclonal mesenchymal stem cells from the step 4) into a culture medium at a cell density of 1000 cells/cm$^2$ in culture for passage 1; and
   6) subculturing the monoclonal mesenchymal stem cells for passages 2 to 8,
   wherein the monoclonal mesenchymal stem cells reseeded at a cell density of 1000 cells/cm$^2$ for passages 2 to 8,
   wherein the culture medium in the steps 5) and 6) includes an antioxidant, and wherein the method does not comprise a process of preparing a working cell bank.

\* \* \* \* \*